(12) United States Patent
Li et al.

(10) Patent No.: US 9,933,319 B2
(45) Date of Patent: Apr. 3, 2018

(54) ACOUSTIC AMBIENT TEMPERATURE AND HUMIDITY SENSING

(71) Applicant: INVENSENSE, INC., San Jose, CA (US)

(72) Inventors: Xiang Li, Mountain View, CA (US); Omid Oliaei, Los Altos, CA (US); Julius Ming-Lin Tsai, San Jose, CA (US); Baris Cagdaser, Sunnyvale, CA (US); Martin Lim, San Mateo, CA (US)

(73) Assignee: INVENSENSE, INC., San Jose, CA (US)

( * ) Notice: Subject to any disclaimer, the term of this patent is extended or adjusted under 35 U.S.C. 154(b) by 402 days.

(21) Appl. No.: 14/684,711

(22) Filed: Apr. 13, 2015

(65) Prior Publication Data
US 2016/0299014 A1 Oct. 13, 2016

(51) Int. Cl.
*G01K 11/24* (2006.01)
*H04B 11/00* (2006.01)
*G01K 13/02* (2006.01)
*G01N 29/024* (2006.01)

(52) U.S. Cl.
CPC .............. *G01K 11/24* (2013.01); *G01K 13/02* (2013.01); *G01N 29/024* (2013.01); *H04B 11/00* (2013.01); *G01K 2013/024* (2013.01); *G01N 2291/011* (2013.01); *G01N 2291/014* (2013.01); *G01N 2291/02845* (2013.01); *G01N 2291/02881* (2013.01)

(58) Field of Classification Search
CPC .. G01K 11/24; G01K 13/02; G01K 2013/024; G01N 29/024; G01N 2291/011; G01N 2291/014; G01N 2291/02845; G01N 2291/02881; H04B 11/00
See application file for complete search history.

(56) References Cited

U.S. PATENT DOCUMENTS

| 9,097,638 | B2 * | 8/2015 | Avramescu | G01N 29/022 |
| 2002/0104689 | A1 * | 8/2002 | Kats | G01G 3/13 177/210 R |
| 2004/0050142 | A1 * | 3/2004 | Hok | G01N 29/024 73/23.21 |
| 2008/0146890 | A1 * | 6/2008 | LeBoeuf | A61B 5/0059 600/300 |
| 2009/0184830 | A1 * | 7/2009 | Watabe | G01N 29/024 340/628 |
| 2010/0165146 | A1 * | 7/2010 | Shimono | G11B 19/042 348/231.99 |
| 2010/0217099 | A1 * | 8/2010 | LeBoeuf | A61B 5/00 600/301 |

(Continued)

*Primary Examiner* — Lisa Caputo
*Assistant Examiner* — Philip Cotey
(74) *Attorney, Agent, or Firm* — Amin, Turocy & Watson, LLP

(57) ABSTRACT

Acoustic ambient temperature and humidity sensing based on determination of sound velocity is described, in addition to sensors, algorithms, devices, systems, and methods therefor. An exemplary embodiment employs sound velocity in the determination of ambient temperature and humidity. Provided implementations include determinations of sound velocity based on time of flight of a coded acoustic signal and/or based on resonance frequency of a Helmholtz resonator.

7 Claims, 22 Drawing Sheets

(56) References Cited

U.S. PATENT DOCUMENTS

| | | | | |
|---|---|---|---|---|
| 2011/0239759 A1* | 10/2011 | Cobianu | .............. | G01N 29/022 |
| | | | | 73/335.03 |
| 2012/0036917 A1* | 2/2012 | Avramescu | .......... | G01N 29/022 |
| | | | | 73/24.04 |
| 2015/0192479 A1* | 7/2015 | Jochemczyk | .......... | G01K 13/02 |
| | | | | 73/627 |
| 2015/0260587 A1* | 9/2015 | Zheng | .................. | G01K 11/265 |
| | | | | 374/117 |
| 2015/0346159 A1* | 12/2015 | Husebo | ................ | G01N 17/046 |
| | | | | 73/597 |

* cited by examiner

ACOUSTIC AMBIENT TEMPERATURE AND HUMIDITY SENSING

TECHNICAL FIELD

The subject disclosure relates to ambient temperature and humidity sensing and more particularly to sensors, algorithms, devices, systems, and methods therefor.

BACKGROUND

As integration of component devices of consumer electronics products reduce form factor, further integration of various sensors and components can provide rich and distinguishing feature sets in crowded market such as that for mobile devices. For example, acoustic sensors (e.g. microphones) can be utilized in mobile device applications with environmental sensors (e.g. humidity and/or temperature sensors) integrated into the mobile device.

For devices such as mobile devices having integrated environmental sensors, accurate ambient temperature (T) measurements are required to determine ambient relative humidity (RH), for example, using an integrated humidity sensor, where the ambient temperature information is essential for determining an accurate RH reading. However, in smart mobile devices having integrated environmental sensors, there are numerous internal heat sources in mobile devices that can hinder measurement of ambient temperature.

It is thus desired to provide sensor devices and/or techniques that improve upon these and other deficiencies. The above-described deficiencies are merely intended to provide an overview of some of the problems of conventional implementations, and are not intended to be exhaustive. Other problems with conventional implementations and techniques and corresponding benefits of the various aspects described herein may become further apparent upon review of the following description.

SUMMARY

The following presents a simplified summary of the specification to provide a basic understanding of some aspects of the specification. This summary is not an extensive overview of the specification. It is intended to neither identify key or critical elements of the specification nor delineate any scope particular to any embodiments of the specification, or any scope of the claims. Its sole purpose is to present some concepts of the specification in a simplified form as a prelude to the more detailed description that is presented later.

Various embodiments of the subject disclosure can employ aspects of determining sound velocity to facilitate determining environmental parameters such as ambient temperature and humidity. For instance, acoustic ambient temperature and humidity sensing based on determination of sound velocity is described, in addition to sensors, algorithms, devices, systems, and methods therefor. An exemplary embodiment can employ sound velocity in the determination of ambient temperature and/or humidity. Provided implementations include determinations of sound velocity based on time of flight of a coded acoustic signal and/or based on resonance frequency of a Helmholtz resonator.

In a non-limiting example, exemplary methods are described that can comprise determining ambient sound velocity one or more of ambient temperature or ambient relative humidity based on the ambient sound velocity, in non-limiting aspects. As non-limiting examples, exemplary methods can further comprise determining the ambient sound velocity outside of an encasement/enclosure based on a determined resonance frequency of a Helmholtz resonator within the encasement/enclosure and/or based on a determined time of flight of a coded acoustic signal from a transmitter to a receiver over a predetermined acoustic path length.

Exemplary systems can comprise a memory to store computer-executable components, a processor communicatively coupled to the memory that facilitates execution of the computer-executable components, and one or more of a sound velocity component within an encasement/enclosure and configured to determine ambient sound velocity external to the encasement/enclosure, and/or an environmental sensing component within the encasement/enclosure and configured to determine one or more of an ambient temperature or an ambient relative humidity external to the encasement/enclosure based in part on the ambient sound velocity. In non-limiting aspects, the sound velocity component can comprise a transmitter configured to transmit a coded ultrasonic acoustic signal to a receiver, which in turn can be configured to receive the coded ultrasonic acoustic signal. Thus, an exemplary sound velocity component can be configured to determine the ambient sound velocity based on a determined time of flight of the coded ultrasonic acoustic signal over a predetermined acoustic path length. In other non-limiting aspects, the sound velocity component can comprise or be associated with a Helmholtz resonator within the encasement/enclosure, and the sound velocity component can be configured to determine the ambient temperature external to the enclosure based on the ambient sound velocity.

Moreover, exemplary sensors, sensors, algorithms, devices, and apparatuses, are provided according to one or more aspects of the subject disclosure.

These and other embodiments are described in more detail below.

BRIEF DESCRIPTION OF THE DRAWINGS

Various non-limiting embodiments are further described with reference to the accompanying drawings in which.

DETAILED DESCRIPTION

Overview

Figure 1:
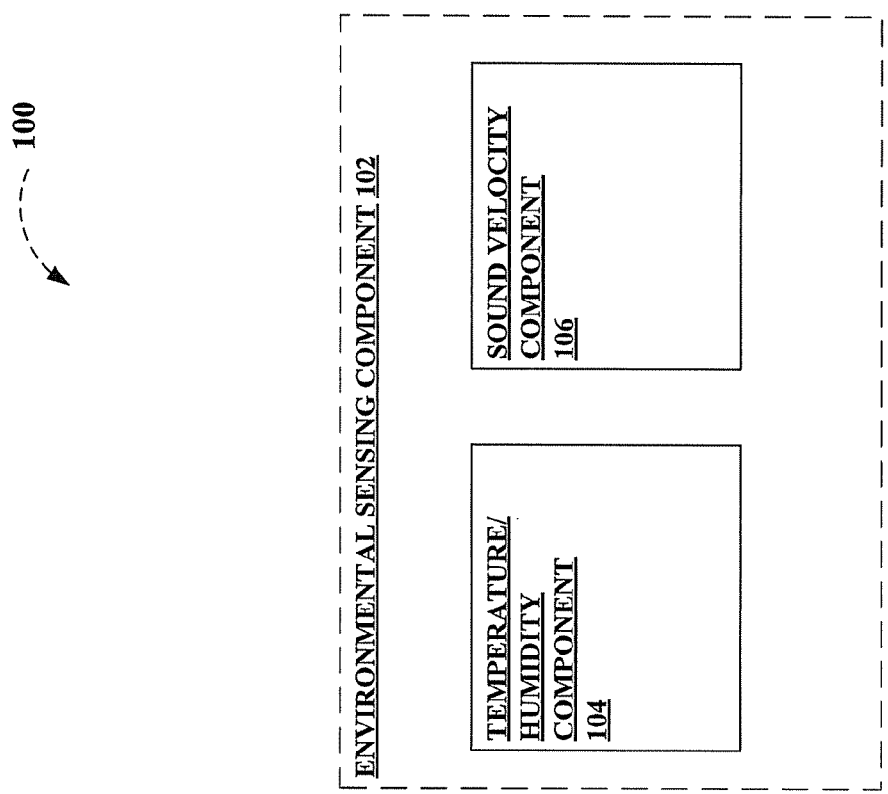
FIG. 1 depicts an exemplary system configured to determine ambient temperature and/or relative humidity, in which non-limiting aspects of the subject disclosure can be practiced.

While a brief overview is provided, certain aspects of the subject disclosure are described or depicted herein for the purposes of illustration and not limitation. Thus, variations of the disclosed embodiments as suggested by the disclosed apparatuses, systems, and methodologies are intended to be encompassed within the scope of the subject matter disclosed herein.

As used herein, microelectromechanical (MEMS) systems can refer to any of a variety of structures or devices fabricated using semiconductor-like processes and exhibiting mechanical characteristics such as the ability to move or deform. For instance, such structures or devices can interact with electrical signals. As a non-limiting example, a MEMS acoustic sensor can include a MEMS transducer and an electrical interface. In addition, MEMS structures or devices can include, but are not limited to, gyroscopes, accelerometers, magnetometers, environmental sensors, pressure sensors, acoustic sensors or microphones, and radio-frequency components.

As described above, integrated environmental sensors of mobile devices can be presented with significant interference from adjacent internal thermal sources, which can shield or obscure them from directly reading ambient temperature (T) and/or ambient relative humidity (RH) values. This can reduce the value of such integrated environmental sensors for applications where ambient T values and/or ambient RH values are of more interest than temperature or humidity values inside of the body, encasement, or enclosure of the mobile devices.

Accordingly, various embodiments of the subject disclosure can determine ambient T and/or RH using more directly measurable ambient physical parameters. For instance, in a non-limiting aspect, measurement of the velocity of sound can be employed to determine ambient T values and/or ambient RH values. As further described herein, ambient T values and/or ambient RH values can be determined based, in part, on ambient sound velocity, which can be shown to be a function of both ambient T and ambient RH.

As a result, in further non-limiting aspects, various embodiments can deduce ambient T values, directly, or from the temperature values obtained by employing integrated temperature sensors. In yet another non-limiting aspect, measurement of the ambient velocity of sound for waves of ultrasound frequency (e.g., greater than about 25 kilohertz (KHz)) can be employed to determine ambient T values and/or ambient RH values. In a further non-limiting aspect, various embodiments can facilitate calibration internal temperature sensors information determined based on the sound velocity, for example, in environments with the extremely high temperature or/and high humidity levels.

Accordingly, as further described herein, various embodiments can determine ambient RH from the ambient T values. For example, as further described herein, ambient T values as provided by various described embodiments can be determined based, in part, on ambient sound velocity, for which, described embodiments can overcome the complexity involved with determining ambient RH from the internal temperature sensor values, which internal temperature sensors also have a humidity dependence.

Exemplary Embodiments

Various aspects or features of the subject disclosure are described with reference to the drawings, wherein like reference numerals are used to refer to like elements throughout. In this specification, numerous specific details are set forth in order to provide a thorough understanding of the subject disclosure. It should be understood, however, that the certain aspects of disclosure may be practiced without these specific details, or with other methods, components, parameters, etc. In other instances, well-known structures, components, circuits, devices, and so on are shown in block diagram form to facilitate description and illustration of the various embodiments.

As mentioned, various embodiments of the subject disclosure can determine ambient T and/or RH using more directly measurable ambient physical parameters. As used herein, reference to determination and/or sensing of ambient relative humidity can refer to facilitation of reasonably accurate determination of relative humidity of the ambient based on sensed variables including, but not limited to, local temperature, local humidity, and/or ambient sound velocity, depending on context, according to relationships described herein. For instance, in a non-limiting aspect, measurement of the velocity of sound (e.g., ambient sound velocity) can be employed to determine ambient T values and/or ambient RH values. For example, FIG. 1 depicts an exemplary embodiment of a system 100 configured to determine ambient temperature and/or relative humidity, in which non-limiting aspects of the subject disclosure can be practiced. System 100 and/or portions or components thereof can be integrated or associated with an electronic device such as a mobile device, for example, as further described herein. System 100 can comprise an environmental sensing component 102, which can comprise one or more of a temperature and/or humidity component 104 and/or a sound velocity component 106, as further described below regarding FIGS. 18-19, for example. According to various exemplary implementations, temperature and/or humidity component 104 can comprise a solid semiconductor based device, which can provide local temperature and/or local humidity information at the sensing point or location of the device, for example, as further described below regarding FIGS. 3-4.

Figure 2:
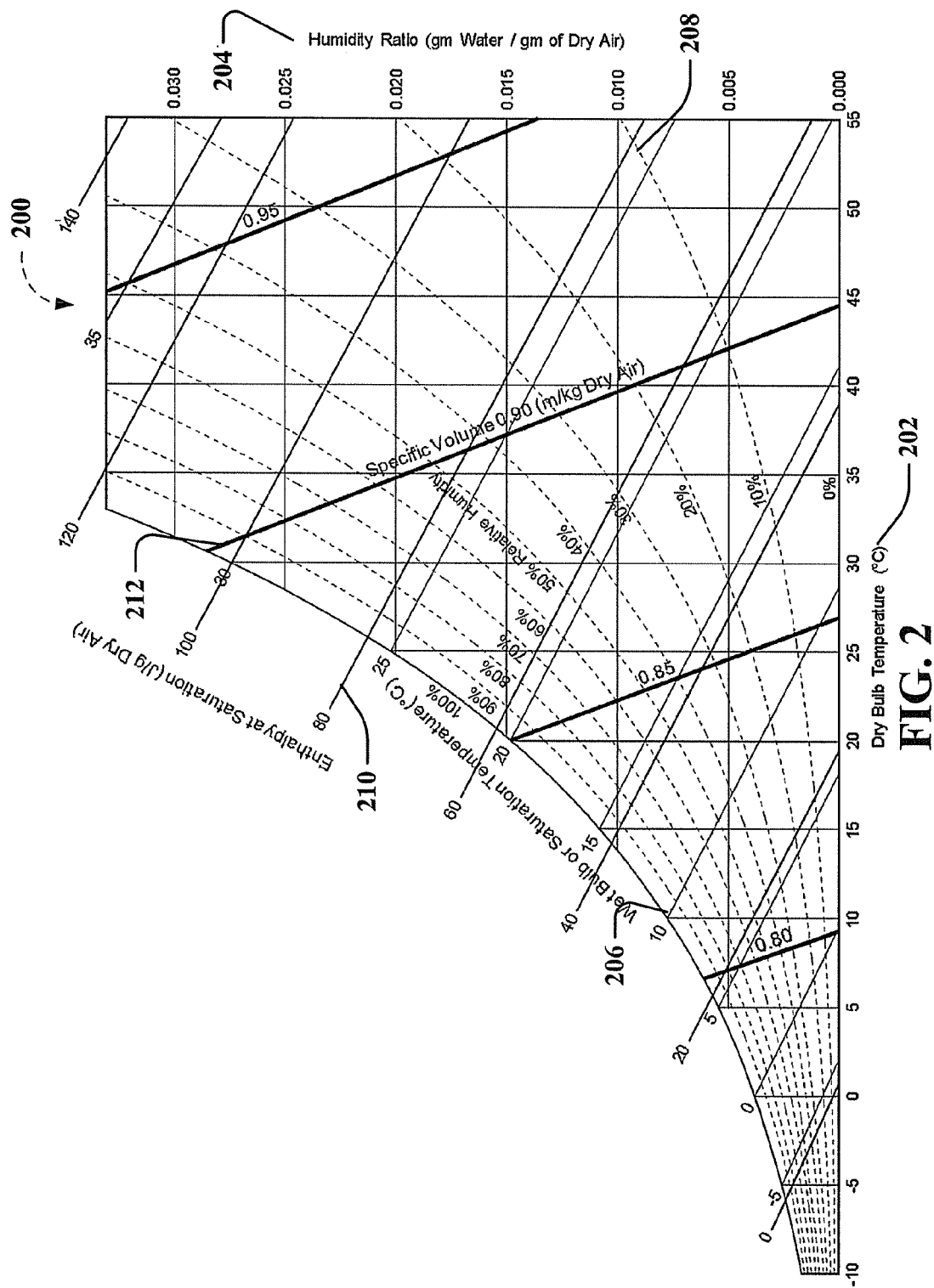
FIG. 2 depicts an exemplary psychrometric chart for an atmospheric air, water vapor system, to demonstrate aspects of the subject disclosure.

In a non-limiting aspect, measurement of the ambient velocity of sound can be employed to determine ambient T values and/or ambient RH values, for example, directly or based in part on values of temperature and/or humidity provided by temperature and/or humidity sensors. For example, FIG. 2 depicts an exemplary psychrometric chart 200 for an atmospheric air, water vapor system, for the purposes of illustration, and not limitation, of various non-limiting aspects of the subject disclosure. The psychrometric chart of FIG. 2 illustrates the relationship of several physical parameters for a gas-vapor mixture, here, an atmospheric air, water vapor system. For instance, FIG. 2 plots dry bulb temperature 202, humidity ratio 204 or absolute humidity in weight, wet bulb or saturation temperature 206, and relative humidity 208, as well as enthalpy at saturation 210 and specific volume 212.

Figure 3:
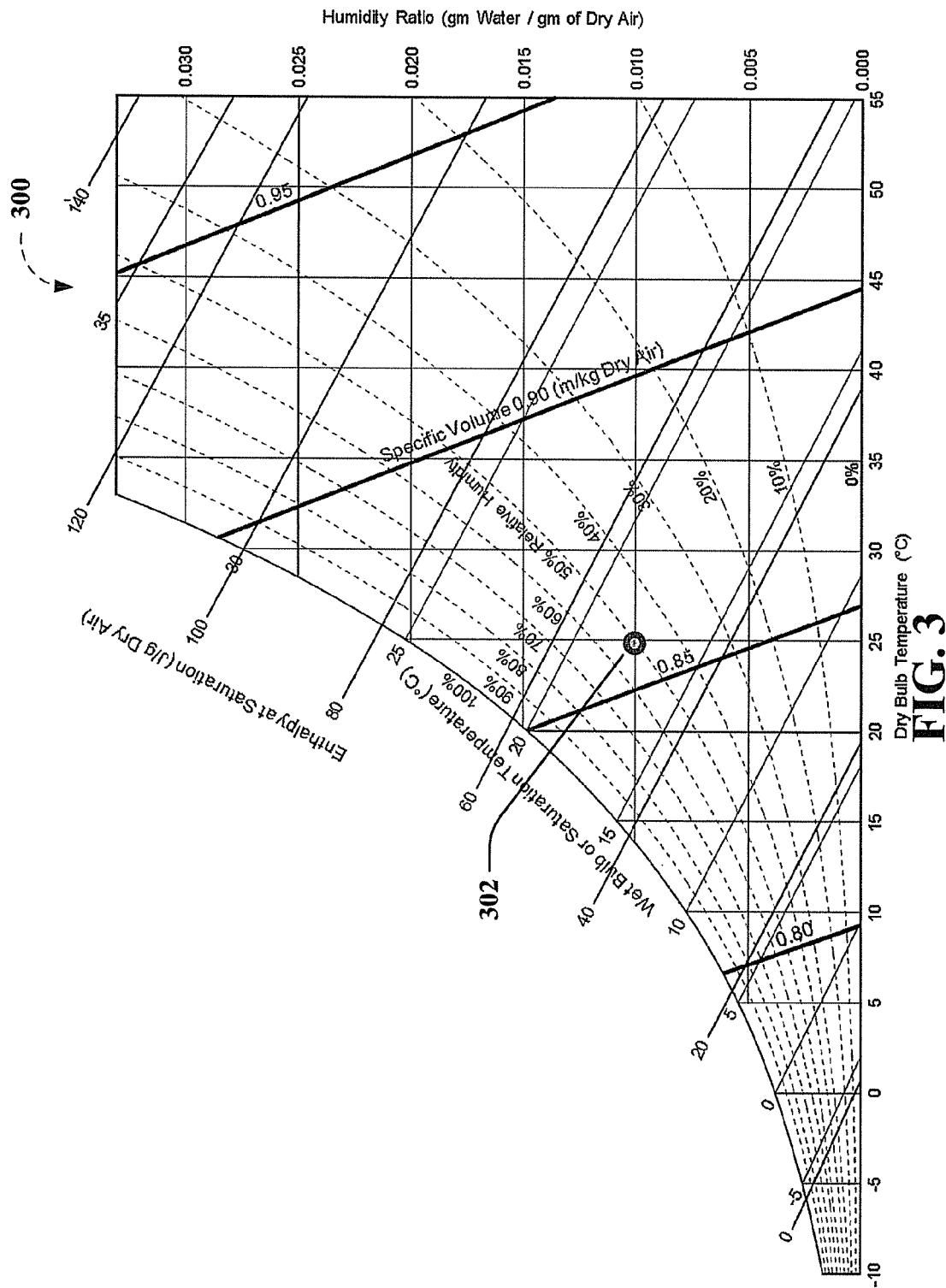
FIG. 3 depicts exemplary psychrometric chart annotated with an exemplary operating point, that can represent environmental conditions of a particular point in space having physical characteristics referred to as ambient herein.

It is to be understood that, as used herein, the particular described examples are provided as an aid to further understanding various aspects of the disclosed subject matter. Thus, reference to particular values, depictions, and the like are not intended to limit the scope of claims appended hereto. For example, FIG. 3 depicts exemplary psychrometric chart 300 annotated with an exemplary operating point 302. As can be seen in FIG. 3, once fixed in the exemplary psychrometric chart 300, the exemplary operating point 302 can be characterized by any and all of the several physical parameters for the gas-vapor mixture (e.g., one or more of dry bulb temperature 202, humidity ratio 204, wet bulb or saturation temperature 206, relative humidity 208, enthalpy at saturation 210, and specific volume 212, etc.). As used herein, exemplary operating point 302 can represent environmental conditions of a particular point in space, for example a point external to an encasement or an enclosure of a device such as a mobile device comprising environmental sensing component 102 or portions thereof.

Figure 4:
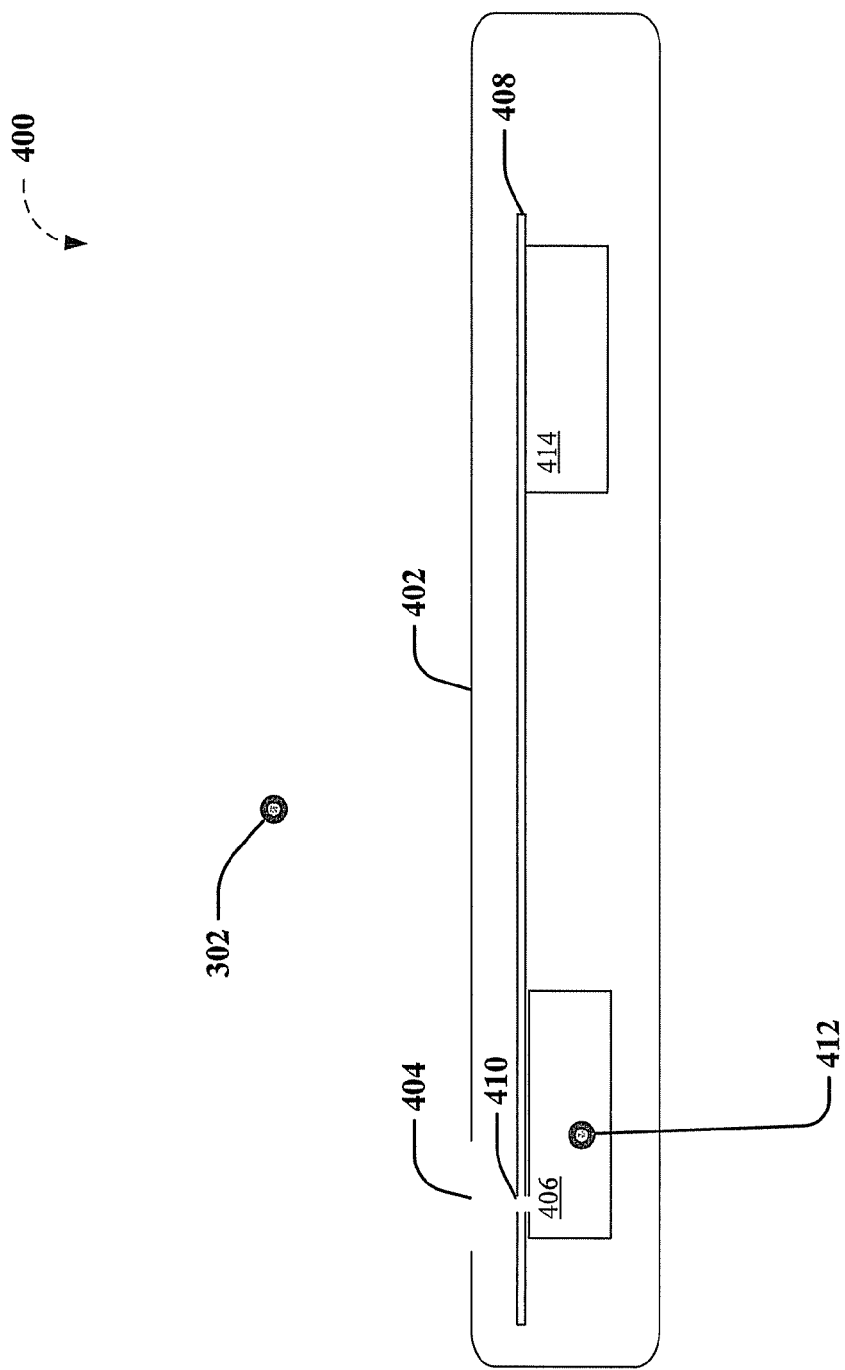
FIG. 4 depicts an exemplary operating environment comprising an encasement or an enclosure that illustrates various non-limiting aspects of the subject disclosure.

For example, FIG. 4 depicts an exemplary operating environment 400 comprising an encasement or enclosure 402 (such as that of a device, a mobile device, etc.) that illustrates various non-limiting aspects of the subject disclosure. Exemplary operating environment 400 can include, but is not limited to, a mobile device comprising or associated with one or more sensors, whether integrated, or otherwise. Note that exemplary operating point 302 is outside of encasement or enclosure 402 and can be characterized by values of the respective physical parameters for the bulk gas-vapor mixture associated with exemplary operating point 302 (e.g., one or more of dry bulb temperature 202, humidity ratio 204, wet bulb or saturation temperature 206, relative humidity 208, enthalpy at saturation 210, and specific volume 212, etc.). As used herein, the term ambient in reference to, for example, physical parameters such as temperature, relative humidity, sound velocity, and so on can refer to such physical parameters associated with exemplary operating point 302. Encasement or enclosure 402 can further comprise a port 404 such as an acoustic port or other structure configured to allow the bulk gas-vapor mixture associated with exemplary operating point 302 to reach an equilibrium state with components inside encasement or enclosure 402. For example, components inside encasement or enclosure 402 can comprise an exemplary sensor 406 affixed to a printed circuit board (PCB) 408 and having an orifice 410 or other means of allowing equilibration of environmental conditions external to encasement or enclosure 402 with exemplary sensor 406.

Accordingly, it can be understood that, while an equilibrium state between physical parameters associated with exemplary operating point 302 and conditions at sensing point 412 within exemplary sensor 406 can be reached, heat generated by other components within encasement or enclosure 402, such as component 414 (e.g., other sensors, memories, processors, etc.) can shield or obscure exemplary sensor 406 from directly reading ambient temperature and ambient relative humidity values associated with exemplary operating point 302. In other words, exemplary sensor 406, comprising a humidity sensor configured to sense conditions at sensing point 412 could be prevented from providing accurate representations of ambient relative humidity at operating point 302, for example, if temperature measurements made at sensing point 412 are used in conjunction with humidity measurements at sensing point 412. This can be due in part to temperature measurements having a sensitivity to relative humidity themselves.

Figure 5:
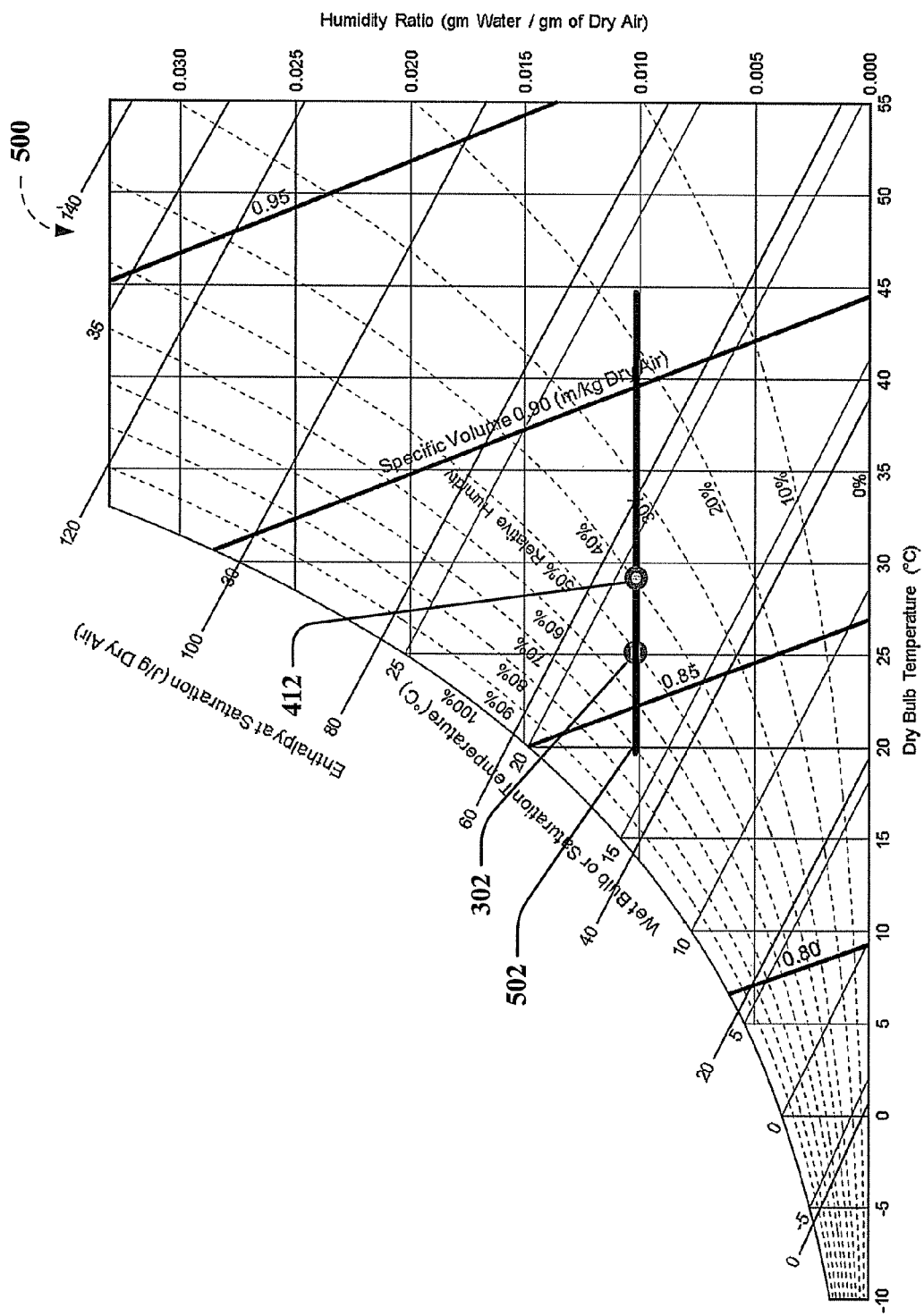
FIG. 5 depicts an exemplary psychrometric chart annotated with an exemplary operating point and an exemplary sensing point, according to aspects of the subject disclosure.

This is illustrated in FIG. 5, which depicts an exemplary psychrometric chart 500 annotated with an exemplary operating point 302 and an exemplary sensing point 412. When integrated temperature and humidity (TH) sensors, such as an exemplary sensor 406, are housed in a cavity or enclosure, such as encasement or enclosure 402, which is connected to, or able to reach equilibrium with, the ambience or exemplary operating point 302, at an equilibrium state, the absolute humidity (AH) values at exemplary operating point 302 should be close to AH values at exemplary sensing point 412 as measured by the integrated TH sensors, assuming the temperature difference between the exemplary operating point 302 and the exemplary sensing point 412 is small compared to their absolute temperatures (e.g., approximately 300° Kelvin (K)). Accordingly, this is depicted graphically in FIG. 5 as an exemplary line of equal absolute humidity 502, on or about which the exemplary operating point 302 and exemplary sensing point 412 can be expected to reside. In addition, because molecular velocity is proportional to the square root of the kinetic energy, which in turn is proportional to the absolute temperature, the molecular velocity at exemplary sensing point 412 and exemplary operating point 302 can be considered as equal under the above assumptions. As a result, the water vapor pressure or absolute humidity at exemplary sensing point 412 and exemplary operating point 302 can also be considered to be equal.

Figure 6:
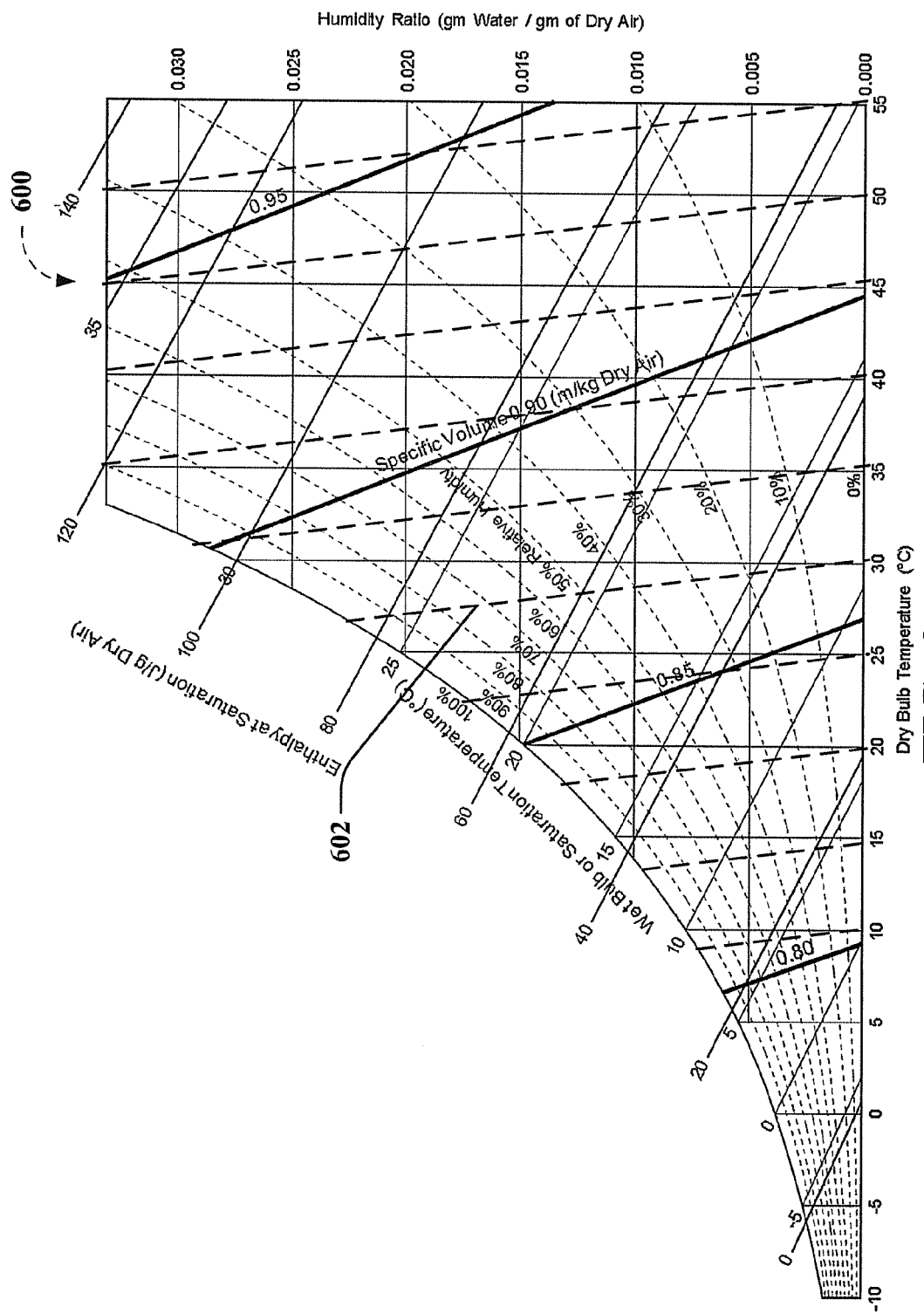
FIG. 6 depicts an exemplary psychrometric chart annotated with lines of constant sound velocity, according to further non-limiting aspects of the subject disclosure.

In addition, FIG. 6 depicts an exemplary psychrometric chart 600 annotated with lines of constant sound velocity 602, according to further non-limiting aspects of the subject disclosure. For instance, as described herein, sound velocity can be shown to be a linear function of both temperature and absolute humidity in weight as indicated in Eqn. (1):

$$v = v(273 \text{ K}, 0\% \ AH) \times \left(1 + 0.5 \times \frac{T_{deg}}{273 \text{ K}}\right)\left(1 + 0.5 \times \frac{11}{18} AH_{mol}\right) \quad (1)$$
$$= v(273 \text{ K}, 0\% \ AH) \times \left(1 + 0.0018 \times \frac{T_{deg}}{\text{K}}\right)\left(1 + 0.0031 \times \frac{AH_{Weight}}{\%}\right)$$

where v is sound velocity, T is temperature, and $AH_{weight}$ is absolute humidity in weight.

For example, various embodiments of the subject disclosure can provide accurate determinations of the ambient temperature, at exemplary operating point 302, for example, by employing sound velocity information. The ambient sound velocity at exemplary operating point 302 is a function of the ambient temperature and absolute humidity. In addition, relative humidity at exemplary sensing point 412 is also a function of temperature sensed at exemplary sensing point 412 and absolute humidity. Accordingly, in the system of exemplary operating environment 400 of FIG. 4 comprising an encasement or enclosure 402, there can be three directly measurable variables (e.g., ambient sound velocity at exemplary operating point 302, and relative humidity and temperature at exemplary sensing point 412), and three unknown variables (e.g., ambient temperature and absolute humidity, at exemplary operating point 302, and absolute humidity at exemplary sensing point 412. To arrive at Eqn. (1), these variables can be related as described herein.

For example, the relationship between relative humidity and temperature and absolute humidity at exemplary sensing point 412 (as well as at exemplary operating point 302) is given by psychrometric charts (e.g., exemplary psychrometric chart 600, etc.). In a non-limiting aspect, as described above, the relationship between absolute humidity at exemplary operating point 302 absolute humidity at exemplary sensing point 412 can be assumed to be equal allowing for appropriate response time for the respective measurements to be taken and when the temperature difference between exemplary operating point 302 and exemplary sensing point 412 is small.

According to FIG. 6 and as described by Eqn. (1), lines of constant sound velocity 602 illustrate qualitatively that when temperature increases the sound velocity v will increase linearly. Lines of constant sound velocity 602 further qualitatively illustrate that sound velocity v will increase when absolute humidity increases linearly, because of the reduction in the average molar mass of the air with more percentage lighter water molecules. For example, according to a further non-limiting aspect, the relationship of sound velocity v with ambient temperature and absolute humidity at exemplary operating point 302 is described herein, regarding Eqns. (2)-(5).

For example, as with sound propagation in solid media, the sound velocity in air can be described by the relationship in Eqn. (2):

$$v = \sqrt{\frac{Y}{\rho}} \quad (2)$$

where Y is the Young's Modulus and ρ is the density of the air. According to the definition of Young's Modulus and the Ideal Gas Law for reversible adiabatic processes or isentropic processes Eqn. (3) provides:

$$pV^\gamma = NkT \quad (3)$$

where V is the volume of a cavity, γ is adiabatic constant, N is the total number of molecules, and k is the Boltzmann constant.

Substituting into Eqn. (2) and solving for sound velocity v, Eqn. (4) provides:

$$v = \sqrt{\frac{\Delta p / s}{\rho}} \quad (4)$$
$$= \sqrt{\frac{\Delta p \; p}{p \; \Delta V / V}}$$
$$= \sqrt{\frac{\gamma \frac{\Delta V}{V} \frac{p}{\Delta V / V}}{\rho}}$$
$$= \sqrt{\frac{\gamma p}{\rho}}$$
$$= \sqrt{\frac{\gamma NkT / V}{m / V}}$$
$$= \sqrt{\frac{\gamma kT}{m_{mol}}}$$

where s is the strain of gas, m is the total mass of the gas, and $m_{mol}$ is the average molar mass of the air.

By supplying values for the various terms and simplifying, Eqn. (5) provides:

$$v = \sqrt{\frac{\gamma kT}{m_{mol}}} \quad (5)$$
$$= \sqrt{\frac{\gamma k(273 \text{ K} + T_{deg})}{29 \frac{\text{g}}{\text{mol}}(1 - AH_{mol}) + 18 \frac{\text{g}}{\text{mol}} AH_{mol}}}$$
$$= \sqrt{\frac{\gamma_{air} k \times 273 \text{ K}}{29 \frac{\text{g}}{\text{mol}}}} \times \sqrt{\frac{1 + \frac{T_{deg}}{273 \text{ K}}}{1 - \frac{29 - 18}{29} \times AH_{mol}}}$$
$$= \sqrt{\frac{\gamma_{air} k \times 273 \text{ K}}{29 \frac{\text{g}}{\text{mol}}}} \times \sqrt{\frac{1 + \frac{T_{deg}}{273 \text{ K}}}{1 - \frac{29 - 18}{29} \times \frac{29}{18} AH_{Weight}}}$$

which can be simplified to yield Eqn. (1).

It is noted that, exemplary results according to Eqn. (1) matches other sources quantitatively to the first order. In addition, qualitative analysis of Eqn. (1) also shows that the constant sound velocity line 602 in the exemplary psychrometric chart 600 should be a straight line drawn from upper left and lower right, as depicted in FIG. 6.

Figure 7:
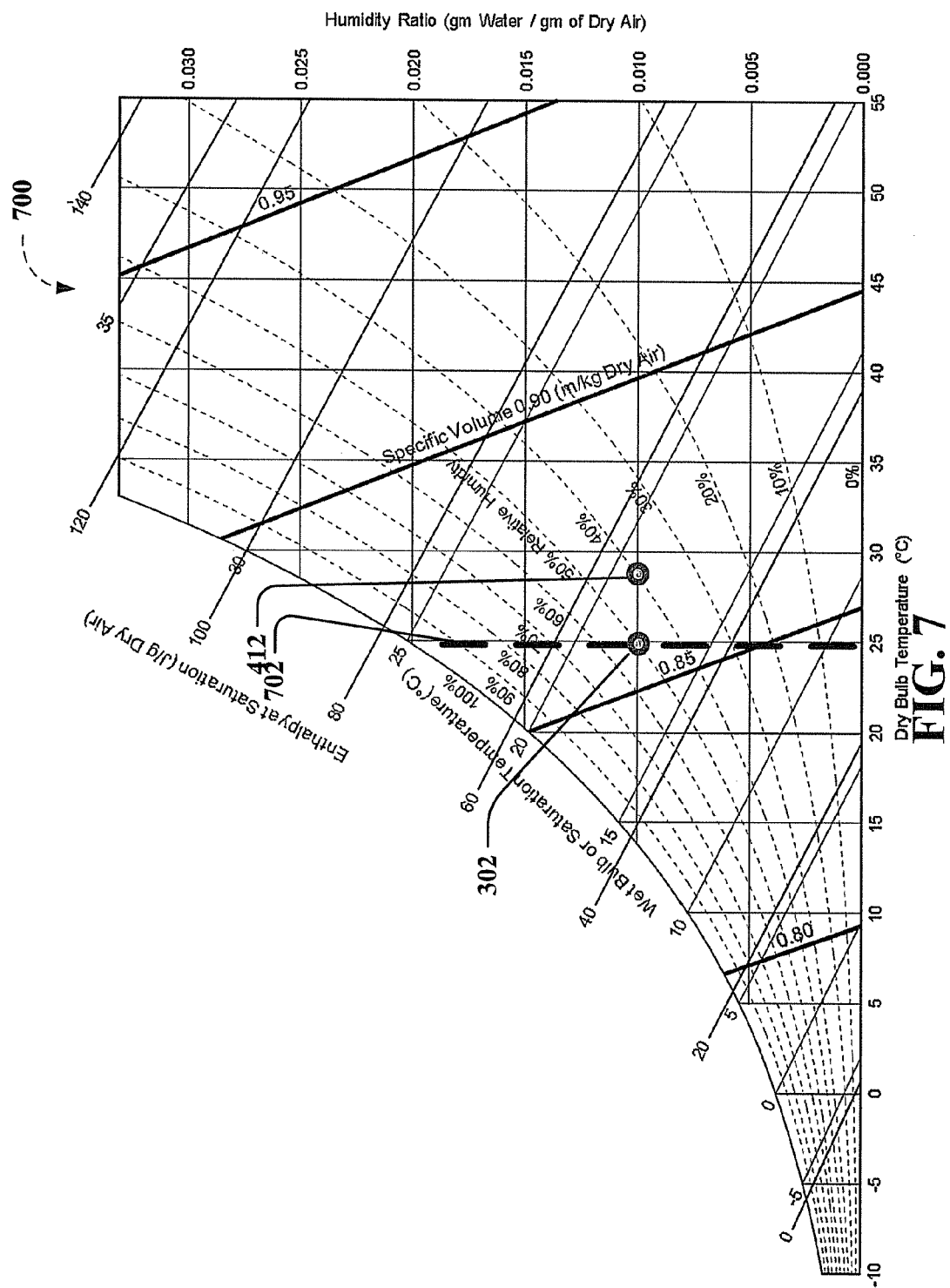
FIG. 7 depicts an exemplary psychrometric chart annotated with a line of constant ambient temperature, according to further non-limiting aspects of the subject disclosure.

FIG. 7 depicts an exemplary psychrometric chart 700 annotated with a line of constant ambient temperature 702, according to further non-limiting aspects of the subject disclosure. Note that ambient temperature at exemplary operating point 302 is not measured directly as provided herein, and thus, according to a non-limiting aspect, ambient temperature at exemplary operating point 302 can be determined based in part on sound velocity and/or temperature sensed at exemplary sensing point 412. However, by determining temperature at exemplary sensing point 412, and employing the relations described above regarding FIG. 6, for example, ambient temperature and ambient relative humidity at exemplary operating point 302 can be determined.

Figure 8:
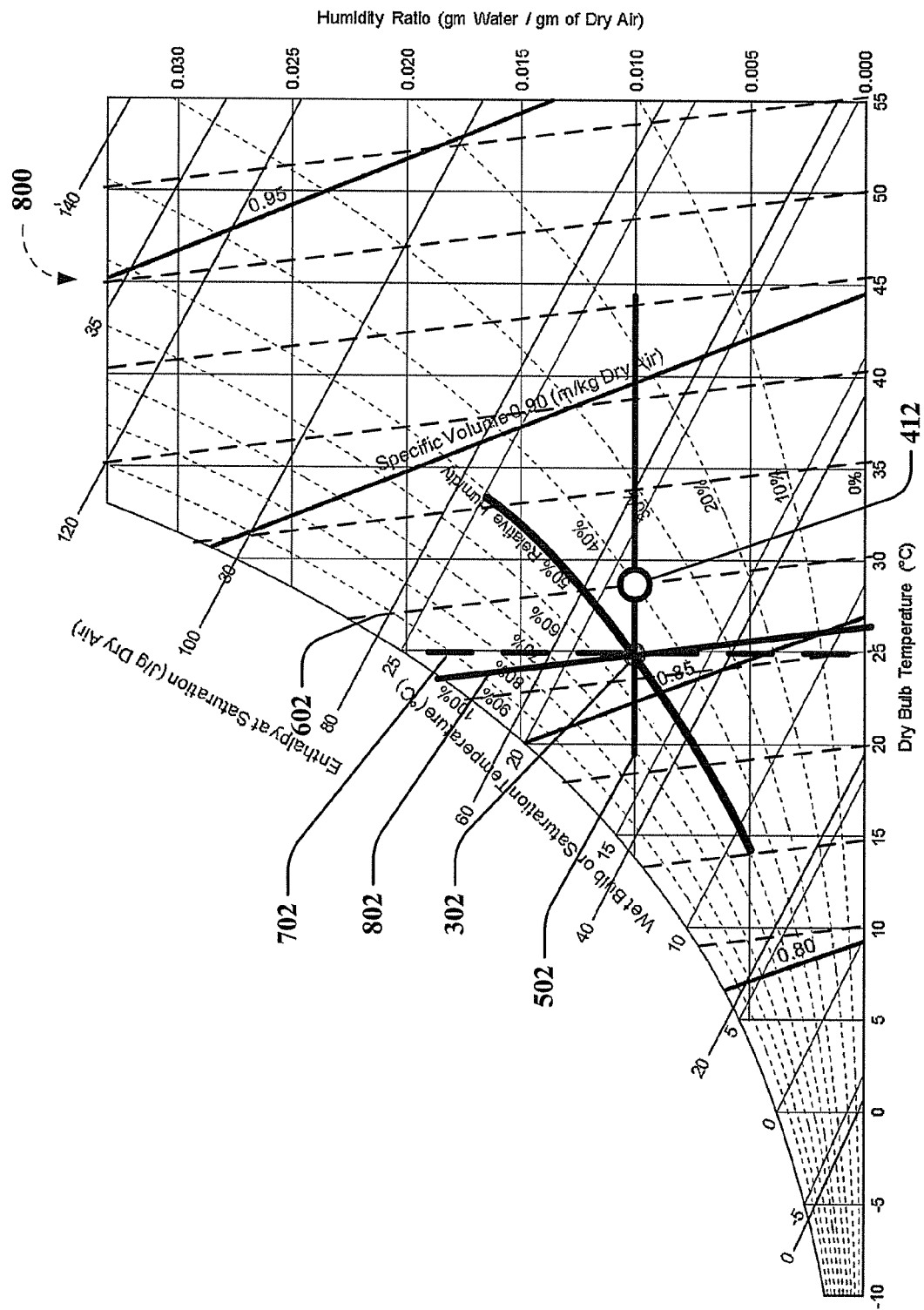
FIG. 8 depicts an exemplary psychrometric chart annotated with a line of constant ambient temperature and lines of constant sound velocity, according to further non-limiting aspects of the subject disclosure.

For instance, FIG. 8 depicts an exemplary psychrometric chart annotated with a line of constant ambient temperature 702 and lines of constant sound velocity 602, according to further non-limiting aspects of the subject disclosure. Thus, by employing the relationship of ambient sound velocity v 802 with ambient temperature at exemplary operating point 302 and the absolute humidity relationship based on measurements at exemplary sensing point 412, under the assumption of small temperature differences and equilibrium with exemplary operating point 302, ambient temperature and ambient relative humidity at exemplary operating point 302 can be determined, according to the relationships as demonstrated in the exemplary psychrometric chart of FIG. 8. As a non-limiting example, interception of the constant sound velocity line 802 and the exemplary line of equal absolute humidity 502 represents the ambient temperature (e.g., 25° Celsius (C) in this case) and ambient RH (e.g., 50% in this case) at exemplary operating point 302.

It is noted that, as depicted in FIG. 8, if the temperature measured at exemplary sensing point 412 was employed alone, versus ambient temperature determined based, in part, on the constant sound velocity line 802, in conjunction with the exemplary line of equal absolute humidity 502, the temperature (e.g., 28° C.) and RH (e.g., 40%) would be an inaccurate representation of the physical parameters associated with exemplary operating point 302 (e.g., temperature and relative humidity). Note further that, by employing information associated with constant sound velocity line 802, various embodiments described herein can provide information suitable for calibration internal temperature sensors (e.g., temperature sensors associated with exemplary sensing point 412, etc), for example, in environments with the extremely high temperature or/and high humidity levels (e.g., regions of the exemplary psychrometric chart where small changes in sensed parameters result in large changes in the parameters to be determined, such as ambient temperature and relative humidity).

Figure 9:
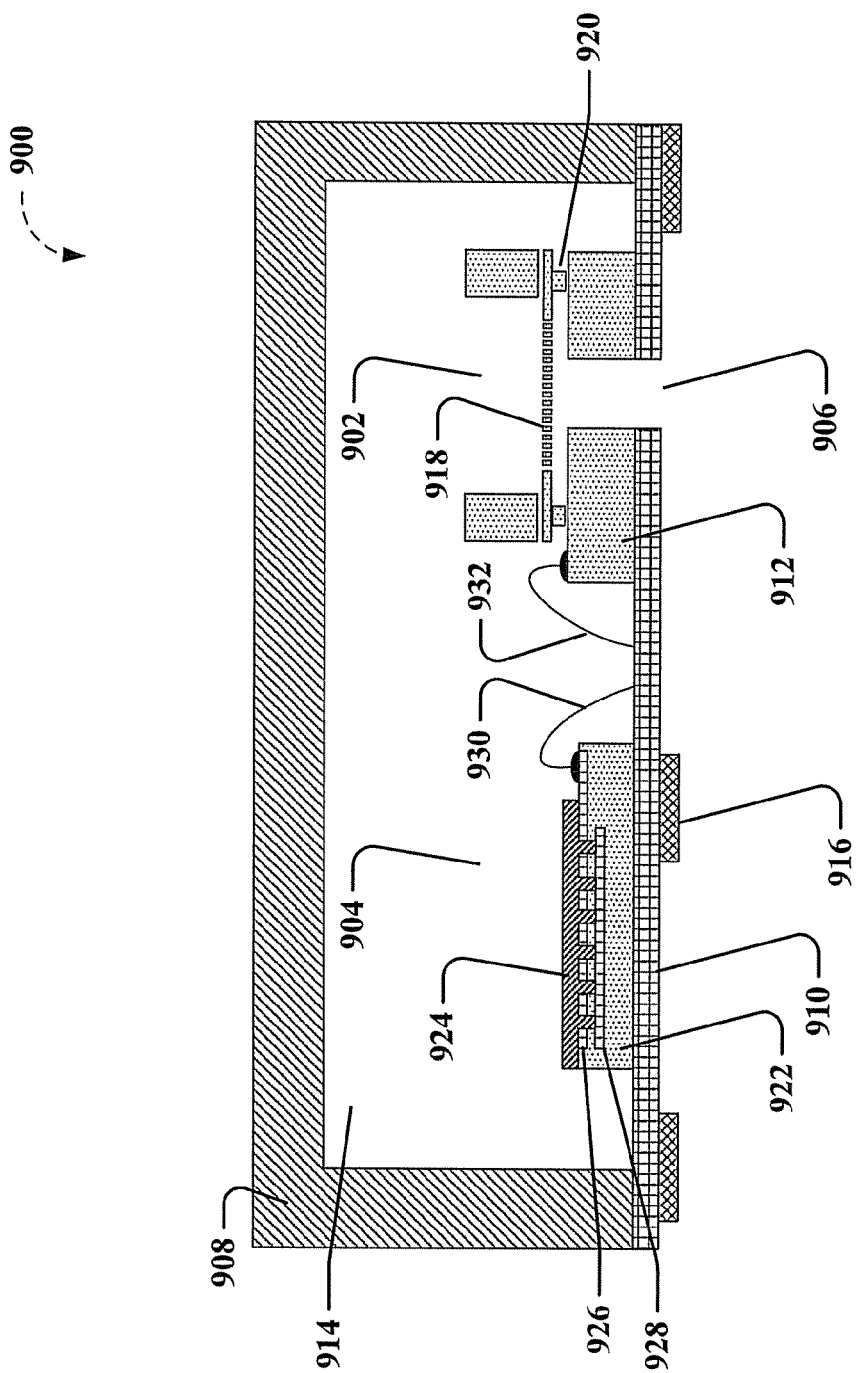
FIG. 9 illustrates an exemplary microelectromechanical systems (MEMS) device, comprising an integrated package, in which an acoustic sensor and an environmental sensor are attached to different application specific integrated circuits (ASICs), that can facilitate performing various non-limiting aspects of the subject disclosure.

Thus, according to various aspects described herein, the disclosed subject matter can provide associated algorithms, systems, and devices and/or components or portions thereof that facilitate determining ambient temperature and relative humidity. As a non-limiting example, exemplary system 100 of FIG. 1 can comprise an environmental sensing component 102, which can comprise one or more of a temperature and/or humidity component 104 and/or a sound velocity component 106. In a further non-limiting example, FIG. 9 illustrates an exemplary microelectromechanical systems (MEMS) device 900, comprising an integrated package, in which an acoustic sensor 902 and an environmental sensor 904 are attached to different application specific integrated circuits (ASICs), that can facilitate performing various non-limiting aspects of the subject disclosure. For example, as described above, components inside encasement or enclosure 402 of FIG. 4, can comprise an exemplary sensor 406 affixed to a PCB 408 and having an orifice 410 or other means of allowing equilibration of environmental conditions external to encasement or enclosure 402 with exemplary sensor 406. Thus, exemplary MEMS device 900 can provide sensing functions associated with exemplary sensor 406, for example, as further described herein.

Accordingly, exemplary MEMS device 900 comprising acoustic sensor 902 and environmental sensor 904 can further comprise a port 906, a lid (or cover) 908, a package substrate 910, an acoustic sensor integrated circuit (IC) substrate 912, and a back cavity 914. Solder 916 can connect exemplary MEMS device 900 to external substrates, such as, for example, PCB 408 having orifice 410 or other means of allowing equilibration of environmental conditions external to encasement or enclosure 402 with exemplary sensor 406. The lid (or cover) 908 and the package substrate 910 can form a "package." While the exemplary acoustic sensor 902 is shown physically separate from exemplary environmental sensor 904, for the purpose of illustration, and not limitation, it is understood that variations of physical configurations of exemplary MEMS device 900 are possible.

According to a non-limiting aspect of exemplary MEMS device 900, acoustic sensor 902 can comprise a microphone, such as, but not limited to, a MEMS microphone. In such embodiments, a sensor element 918 can be a micromachined structure that can move in response to an acoustic signal, e.g., received via port 906. Standoffs 920 can provide a conductive path and can separate the sensor element 918 from the acoustic sensor integrated IC substrate 912. The sensor element 918 and a conductive layer disposed on the acoustic sensor integrated IC substrate 912 can collectively form a capacitor, where capacitance can vary as the distance between the sensor element 918 and the acoustic sensor integrated IC substrate 912 varies due to the movement of the sensor element 918 caused by acoustic pressure vibrations of the acoustic signal.

In further non-limiting aspects of exemplary MEMS device 900, operation of the environmental sensor 904 can use capacitance variation, resistance variation, mass loading, etc. to sense the particular environmental characteristic being sensed. Such characteristics, without limitation, can include temperature, humidity, pressure, biological, and so on. In the exemplary MEMS device 900 of FIG. 9, environmental sensor 904 can comprise an environmental sensor substrate 922, environmental sensing material 924, a capacitor 926, and a heater or temperature sensor 928. As non-limiting examples, capacitor 926 can provide a variable capacitance between metal electrodes in response to a change in a particular environmental characteristic associated with and experienced by environmental sensing material 924.

In non-limiting aspects, temperature and/or humidity component 104 can comprise an internal TH sensor comprising an internal temperature sensor and a RH sensor, where the internal temperature sensor can comprise a temperature sensor sensing the substrate of the RH sensor, a temperature sensor sensing the air temperature near the TH sensors or a combination of both. In further non-limiting aspects, a RH sensor could be a capacitive polymer sensor, either standalone or integrated with a sensor such as microphone and/or one or more gas sensors. Accordingly, environmental sensing material 924 can comprise a humidity sensitive environmental sensing material, which, in conjunction with capacitor 926, facilitates determining humidity, for example, at exemplary sensing point 412. In a further non-limiting example, heater or temperature sensor 928 can comprise a heating element and/or a resistance-based temperature sensor, which can facilitate determining temperature, for example, at exemplary sensing point 412.

In addition, as depicted in FIG. 9, environmental sensor 904 of exemplary MEMS device 900 can be physically and electrically coupled to the environmental sensor substrate 922 comprising the IC substrate. In such case, the environmental sensor substrate 922 comprising an IC substrate can be connected, for example, by wire bond 930, which electrically couples the environmental sensor 904 to the package substrate 910, whereas acoustic sensor IC substrate 912 can be independently electrically coupled to the package substrate 910 through wire bond 932. Accordingly, exemplary MEMS device 900 can provide integrated TH sensors, as further described herein, that can facilitate determining temperature and/or humidity at exemplary sensing point 412. It can be understood that integrated TH sensors, for example, such as depicted in FIG. 9, are merely provided as examples to aid in the understanding of various aspects as described herein, and are not intended to limit the scope of the claims appended hereto.

Thus, having described exemplary integrated TH sensors that facilitate performing various aspects associated with system 100 of FIG. 1, directed to a temperature and/or humidity component 104, the following descriptions provide further non-limiting aspects regarding exemplary sound velocity components 106, suitable for performing further non-limiting aspects associated with system 100 of FIG. 1. For example, in a non-limiting aspect, measurement of the ambient velocity of sound, for example, at exemplary operating point 302, which is a function of both ambient temperature and ambient RH at exemplary operating point 302, can facilitate determining ambient temperature and/or ambient relative humidity values at exemplary operating point 302 from the temperature values with at exemplary sensing point 412 associated with, for example, integrated TH sensors. In a particular non-limiting aspect, measurement of the ambient velocity of sound for waves of ultrasound frequency (e.g., greater than about 25 KHz), for example, at exemplary operating point 302, which is a function of both ambient temperature and ambient RH at exemplary operating point 302, can facilitate determining ambient temperature and/or ambient relative humidity values at exemplary operating point 302 from the temperature values determined at exemplary sensing point 412 associated with, for example, integrated TH sensors.

Figure 10:
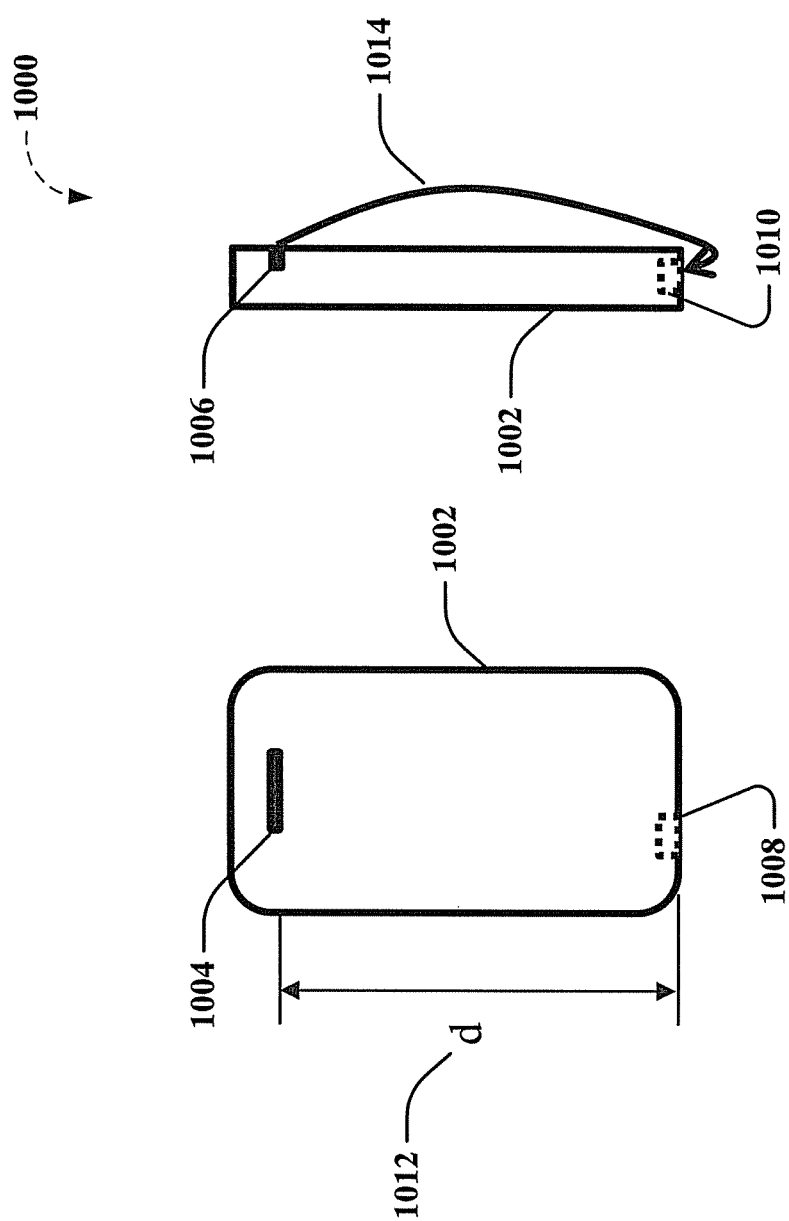
FIG. 10 depicts a plan view and side elevation of an exemplary device that illustrates aspects of determining sound velocity from time of flight (TOF) of an acoustic signal over a known distance in the ambient air.

Accordingly, in various non-limiting embodiments, the subject disclosure provides systems and devices and/or components or portions thereof and associated algorithms suitable for determining ambient temperature and relative humidity using ambient sound velocity by determining time of flight of an acoustic signal over a known distance, for example, by employing a synchronized transmitter and receiver (e.g., a speaker and microphone of a smart mobile device, etc.). As a non-limiting example, FIG. 10 depicts a plan view and side elevation of an exemplary device 1000 that illustrate aspects of determining sound velocity by determining time of flight of an acoustic signal over a known distance in the ambient air (e.g., at exemplary operating point 302). For example, exemplary device 1000 can comprise an exemplary smart mobile device, including, but not limited to, a smart phone, which can comprise an enclosure 1002, such as encasement or enclosure 402 of FIG. 4, for example. As described above, there can be numerous heat sources within enclosure 1002 that can hinder accurate determinations of ambient temperature at exemplary operating point 302 using temperature sensors located within enclosure 1002. Accordingly, as described herein, various non-limiting embodiments of the subject disclosure can provide determinations of ambient temperature (and/or ambient relative humidity) at exemplary operating point 302, based in part on determinations of sound velocity of the ambient in conjunction with temperature values determined at exemplary sensing point 412 associated with, for example, integrated TH sensors.

Accordingly, enclosure 1002 can comprise a first port or opening 1004 that facilitates transmission of an acoustic signal from a transmitter 1006 (e.g., a speaker, etc.) and a second port or opening 1008 that facilitates reception of the acoustic signal from the transmitter 1006 at a receiver 1010 (e.g., microphone, etc.). As depicted in FIG. 10, the first port or opening 1004 can be separated from the second port or opening 1008 by a predetermined distance, d, 1012, which can determine, in part, an acoustic path 1014.

Figure 11:
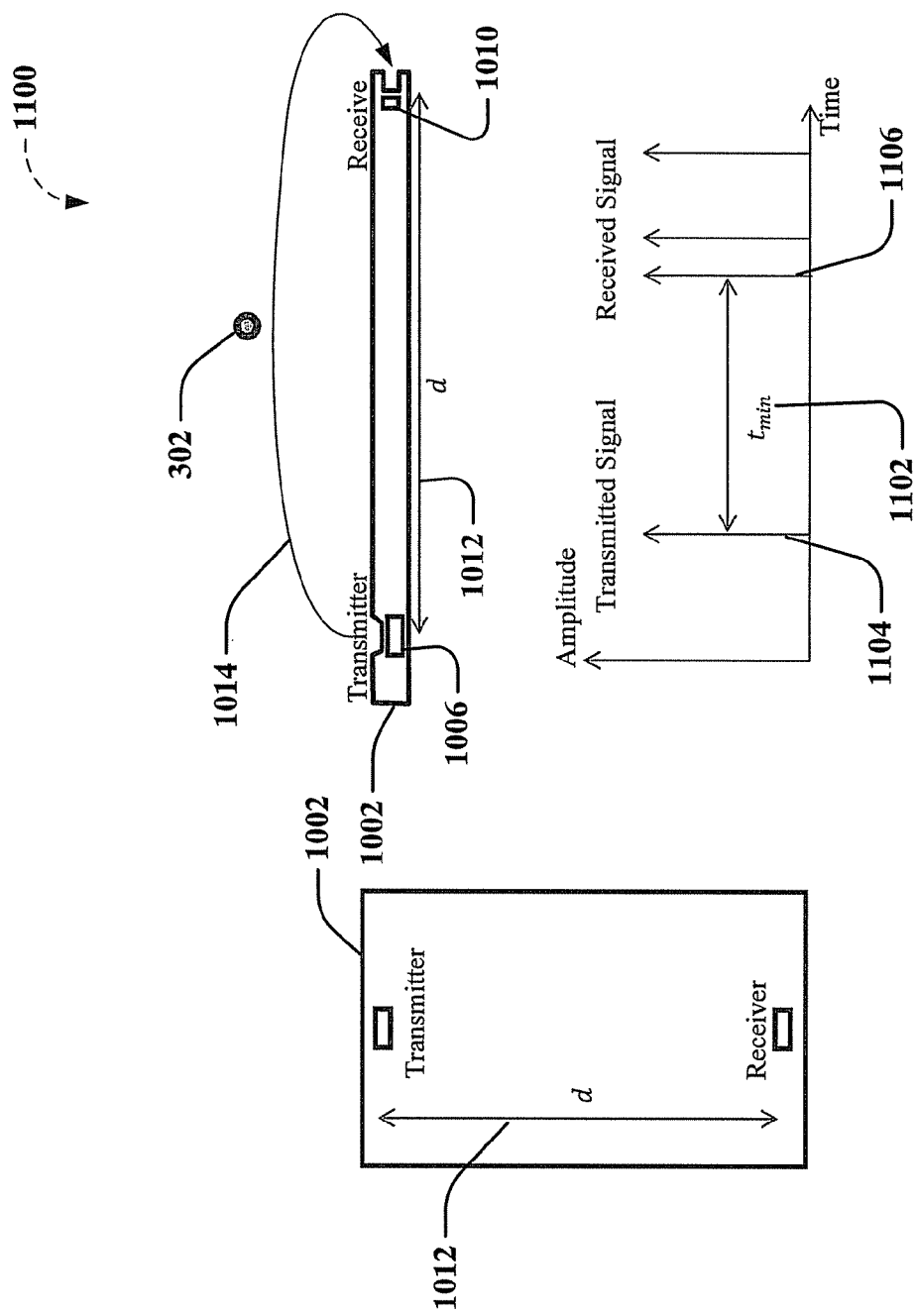
FIG. 11 depicts an exemplary system that facilitates performing non-limiting aspects of the subject disclosure directed to determination of sound velocity.

Similarly, FIG. 11 depicts an exemplary system 1100 that facilitates performing non-limiting aspects of the subject disclosure directed to determination of sound velocity. While not depicted in FIG. 11 for clarity, it can be presumed that exemplary sensing point 412 can be located at a receiver 1010 (e.g., microphone, etc.), for example, such as described above regarding of exemplary MEMS device 900 of FIG. 9. As sound velocity is a strong function of temperature and weak function of humidity, transmitter 1006 (e.g., a speaker, etc.) and receiver 1010 (e.g., microphone, etc.) separated by the known predetermined distance, d, 1012 (or acoustic path 1014) can be employed to determine ambient sound velocity (e.g., at exemplary operating point 302), for example, by sending a coded signal from transmitter 1006 (e.g., a speaker, etc.) to a synchronized receiver 1010 (e.g., microphone, etc.) to determine the time of flight, $t_{min}$, 1102 based on the time difference between the transmitted signal 1104 and the received signal 1106, according to Eqn. (6) as follows:

$$t = \frac{d}{c} \text{ or } T = \frac{-b + \sqrt{b^2 - 4ac}}{2a} \qquad (6)$$

where: $a \approx 5.573 \times 10^{-47} - 7.824 \times 10^{-4 \times AH}$ $b \approx 0.6067 + 0.1495874 \times AH$ $c \approx 331.452 - C - 2.835149 \times AH^2 + 51.471936 \times AH$ d is the acoustic path, C is the sound velocity, and AH is the molar fraction of water vapor.

From the time of flight, t, 1102 and a predetermined or known acoustic path 1014, the ambient temperature can be determined from Eqn. (6), for example, by gathering the absolute humidity (or molar fraction of water vapor) from a humidity sensor, for example, as described herein, which can derive AH associated with exemplary operating point 302 based on sensor temperature and sensor RH at exemplary sensing point 412. As the ambient sound velocity, C, depends on a known or predetermined acoustic path 1014, d, non-limiting embodiments that determine the ambient sound velocity measurement according to Eqn. (6) can be configured to minimize variations in the length of acoustic path 1014, d. This can minimize associated error in the determination of the ambient sound velocity, C, and, in turn, can minimize associated error in the determination of the ambient temperature and relative humidity, for example, at exemplary operating point 302.

Figure 12:
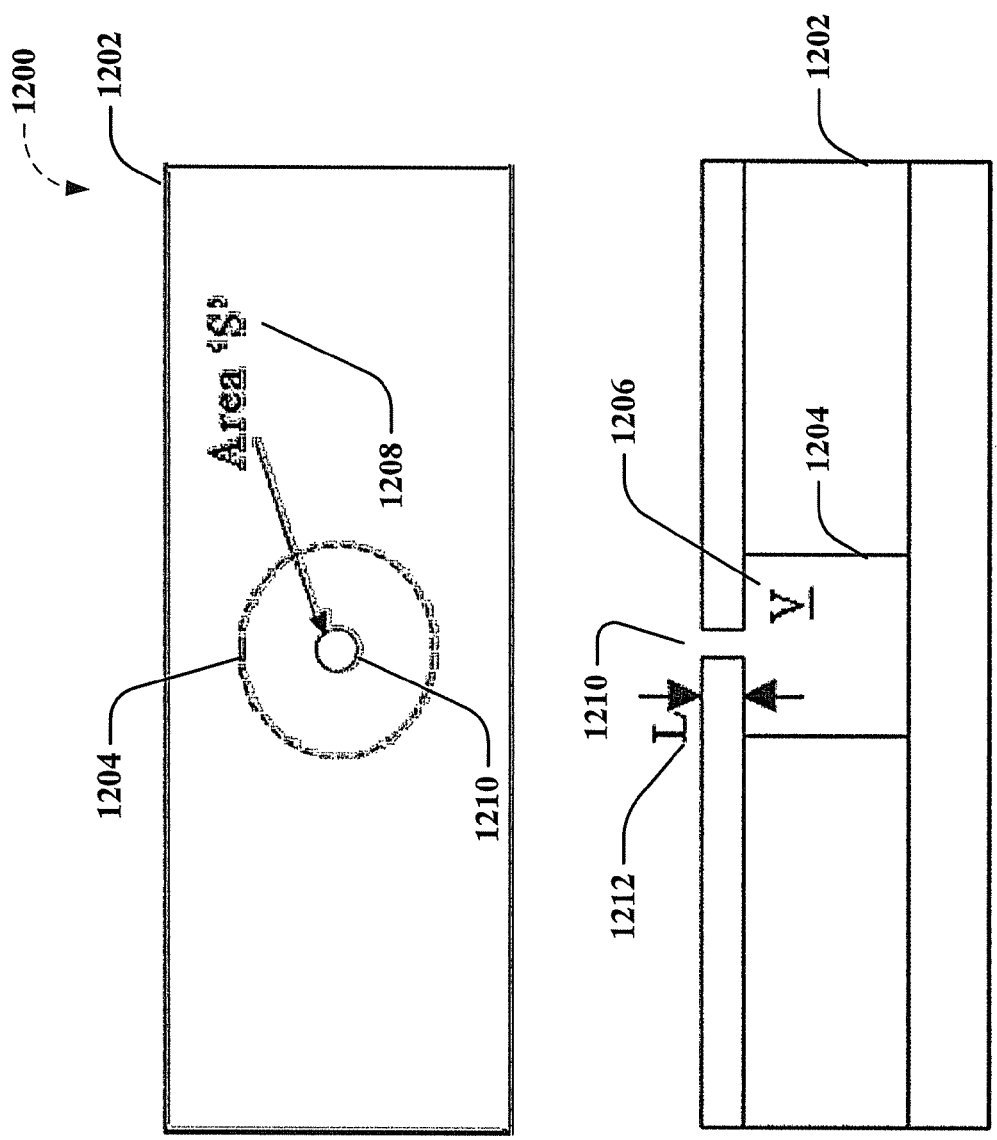
FIG. 12 depicts a plan view and side elevation of another exemplary device that facilitates performing non-limiting aspects of the subject disclosure directed to determination of sound velocity based on a determination of resonant frequency of a Helmholtz resonator.

Accordingly, in further non-limiting embodiments, the subject disclosure provides systems and devices and/or components or portions thereof and associated algorithms suitable for determining ambient temperature and relative humidity using ambient sound velocity by determining the resonant frequency of a Helmholtz resonator (HR). For instance, FIG. 12 depicts another exemplary device 1200 that facilitates performing non-limiting aspects of the subject disclosure directed to determination of sound velocity based on a determination of resonant frequency of a Helmholtz resonator 1202. Helmholtz resonance is a physical phenomenon characterized by air resonance in a cavity. Resonant frequency of a Helmholtz resonator (e.g., HR 1202) depends on its geometrical dimensions and velocity of sound. For example, for a Helmholtz resonator, such as HR 1202 of FIG. 12 comprising a cavity 1204 with volume, V, 1206, area 1208, S, of an opening 1210 to the cavity 1204, and thickness 1212, L, of the neck 1210, the relationship between sound velocity, c, and the resonance frequency $f_h$ of HR 1202 can be determined according to Eqn. (7) as follows:

$$f_h = \frac{c}{2\pi}\sqrt{\frac{S}{LV}} \qquad (7)$$

Accordingly, in an aspect, various non-limiting embodiments comprising a HR (e.g., HR 1202) having specified dimensions can facilitate determination of sound velocity based, in part, on a determination of the resonant frequency of a HR (e.g., HR 1202). For example, by determining resonant frequency a Helmholtz resonator, such as HR 1202 of FIG. 12, and solving Eqn. (7), the sound velocity, c, can be determined. It can be understood that determination of the resonant frequency of a HR (e.g., HR 1202), and thus, the determination of sound velocity, can be relatively reliable if dimensions of the cavity (e.g., cavity 1204) associated with the HR (e.g., HR 1202) do not change significantly. In addition, the temperature of air in the cavity (e.g., cavity 1204), for example, such as at exemplary sensing point 412, might not match that of the ambient temperature due to internal thermal sources and the time lag between cavity and ambient temperature, such as described above regarding FIG. 4. However, a Helmholtz resonator, such as HR 1202, can be fabricated as a MEMS device, which can measure air temperature (e.g., at exemplary operating point 302) directly according to various aspects described herein, and with high sensitivity. In addition, while, for purposes of illustration, and not limitation, transduction employing HR 1202 is demonstrated as comprising one opening 1210, the disclosed subject matter can employ any of a Helmholtz resonator configurations, including, but not limited to variations in Helmholtz resonator shapes, volumes, materials, numbers of openings, and so on, etc. For instance, particular non-limiting implementations can comprise a Helmholtz resonator comprising one or more openings 1210.

Figure 13:
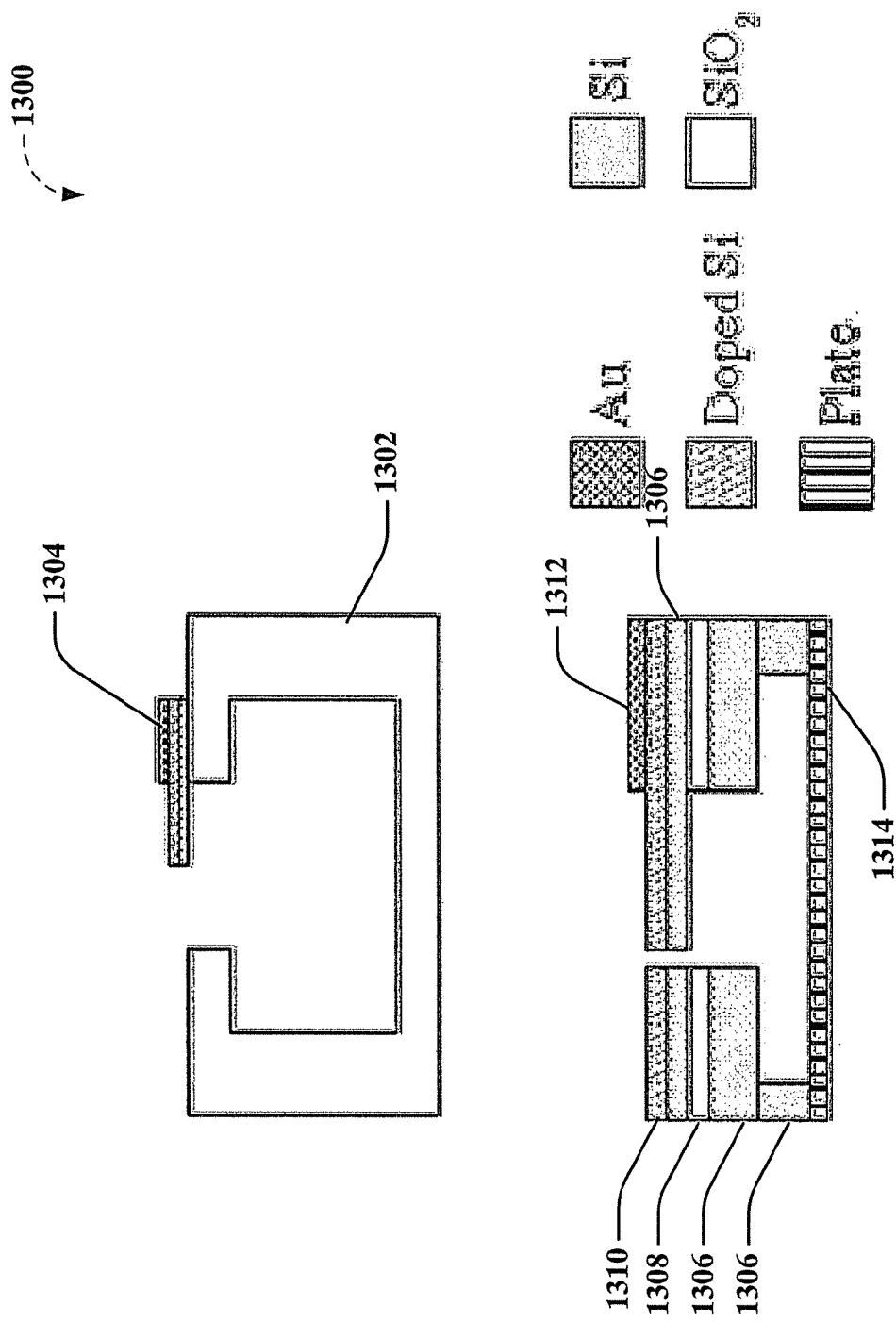
FIG. 13 depicts an exemplary conventional MEMS Helmholtz resonator comprising a piezoresistive cantilever that facilitates performing non-limiting aspects of the subject disclosure directed to determination of sound velocity.
Figure 14:
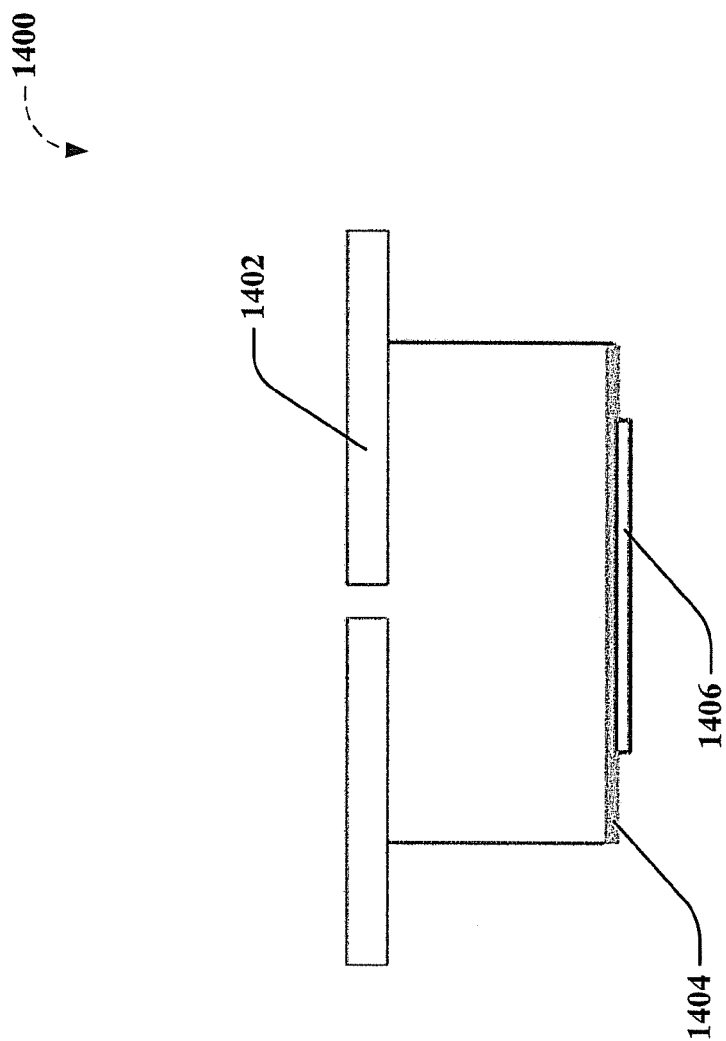
FIG. 14 depicts another exemplary Helmholtz resonator, suitable for MEMS fabrication, comprising a compliant backplate and piezoelectric material that can facilitate performing non-limiting aspects of the subject disclosure directed to determination of sound velocity.

As another non-limiting example, FIG. 13 depicts an exemplary conventional MEMS Helmholtz resonator 1302 comprising a piezoresistive cantilever 1304 that facilitates performing non-limiting aspects of the subject disclosure directed to determination of sound velocity. While, for purposes of illustration, and not limitation, transduction employing Helmholtz resonator 1302 is demonstrated using piezoresistive cantilever 1304, the disclosed subject matter can employ any of a number of transduction methods, including, but not limited to, piezoresistive, piezoelectric, capacitive, and/or other techniques. Accordingly, a MEMS HR 1302 can be constructed as depicted in FIG. 13 comprising a fabrication of silicon 1306, Si, silicon dioxide 1308, $SiO_2$, doped silicon 1310, and gold 1312, Au, upon a substrate 1314. As a further non-limiting example, FIG. 14 depicts another exemplary Helmholtz resonator 1402, suitable for MEMS fabrication, comprising a compliant backplate 1404 and piezoelectric material 1406 that can facilitate performing non-limiting aspects of the subject disclosure directed to determination of sound velocity. According to various non-limiting aspects, a MEMS Helmholtz resonator, for example, such as MEMS HR 1302, HR 1402, etc., can be employed to facilitate the determination of the resonant frequency of the Helmholtz resonator, and thus, can facilitate the determination of sound velocity.

As described above, a Helmholtz resonator, such as HR 1202, can be fabricated as a MEMS device, which can measure air temperature (e.g., at exemplary operating point 302) directly according to various aspects described herein, and with high sensitivity. For example, a Helmholtz resonator, such as HR 1202, etc., can directly measure ambient air temperature with a fast response time due to the fast heat exchange (e.g., between a body of ambient air and a body of air within a cavity (e.g., cavity 1204) associated with the HR (e.g., HR 1202)), while providing a wide range of relatively linear measurements and high sensitivity due to the large variation of sound velocity as a function of temperature. In addition, while the resonant frequency may be sensitive to external objects (e.g., physical shock, obstructions, etc.), the provided measurements are relatively insensitive to radiation.

Figure 15:
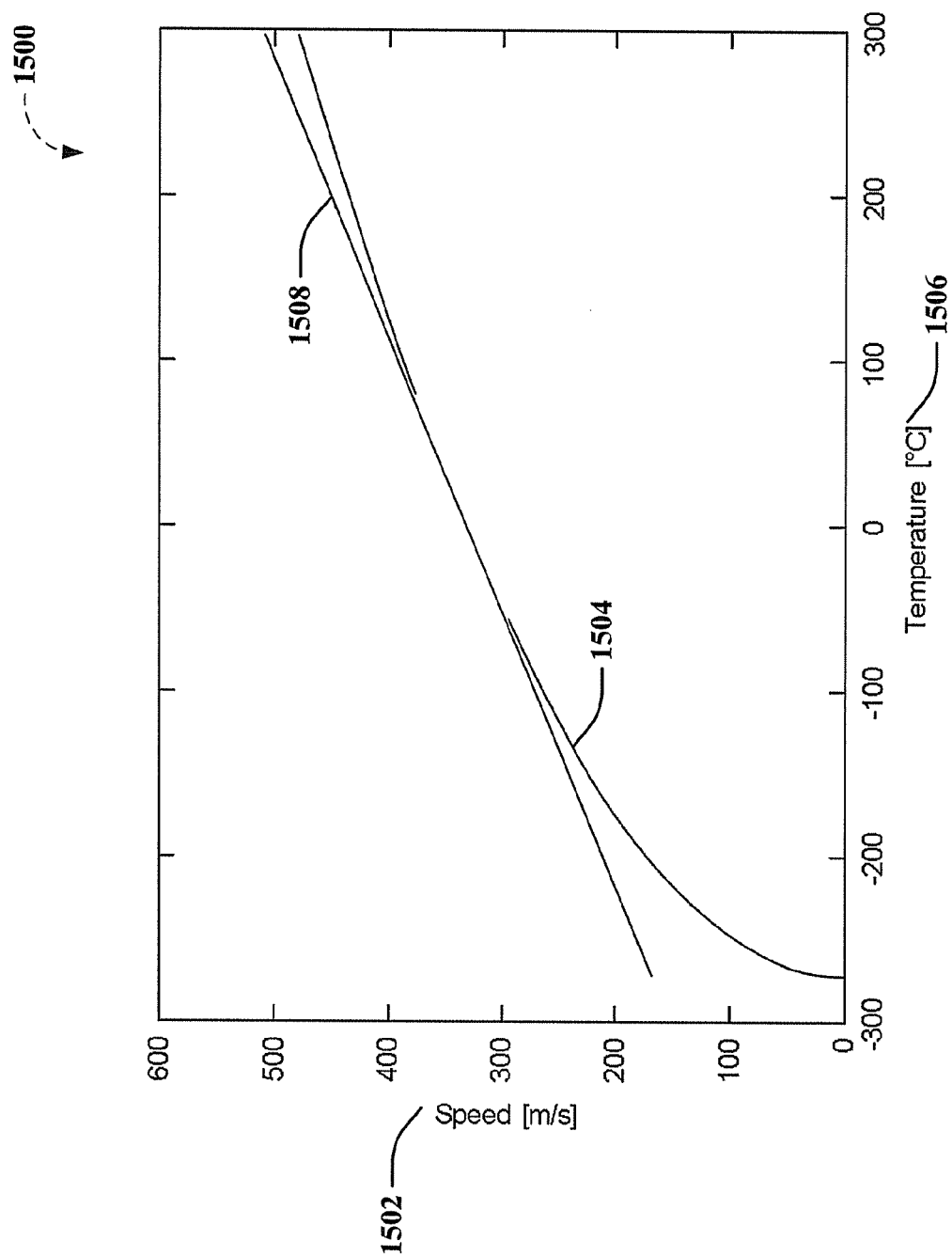
FIG. 15 depicts the speed of sound in dry air as a function of temperature.

For example, FIG. 15 depicts the speed of sound 1502 in dry air, based on heat capacity ratio 1504, as a function of temperature 1506. According to the relationships in Eqns. (8)-(9), below, the relationship of temperature and sound velocity can be approximated by a truncated Taylor expansion 1508 as given in Eqn. (10).

$$c_{ideal} = \sqrt{\gamma\frac{p}{\rho}} = \sqrt{\frac{\gamma RT}{M}} = \sqrt{\frac{\gamma kT}{M}} \qquad (8)$$

$$c_{air} = 331.3\frac{\text{m}}{\text{s}}\sqrt{1 + \frac{\vartheta°\text{ C.}}{273.15°\text{ C.}}} \qquad (9)$$

where k is the Boltzmann constant, γ is the Adiabatic index of approximately 1.403 for air, m is the mass of a single molecule, R is the molar gas constant, T is the absolute temperature in degrees Kelvin, and θ is the temperature in degrees Celsius.

$$c_{air} = (331.3 + 0.606° \text{ C}^{-1} \cdot \vartheta)\frac{\text{m}}{\text{s}} \qquad (10)$$

As depicted in FIG. 15, for moderate temperatures, sound velocity as a function of temperature is relatively linear as approximated in Eqn. (10). Moreover, determination of temperature from sound velocity provides a relatively high degree of sensitivity due to the large variation of sound velocity as a function of temperature. For example, from −25° C. to +35° C., sound velocity varies from approximately 315.77 meters per second (m/s) to about 351.88 m/s at sea level. In addition, the variation of frequency of a Helmholtz resonator is ideally suited to facilitate determination of temperature based on measurements of resonance frequency.

Figure 16:
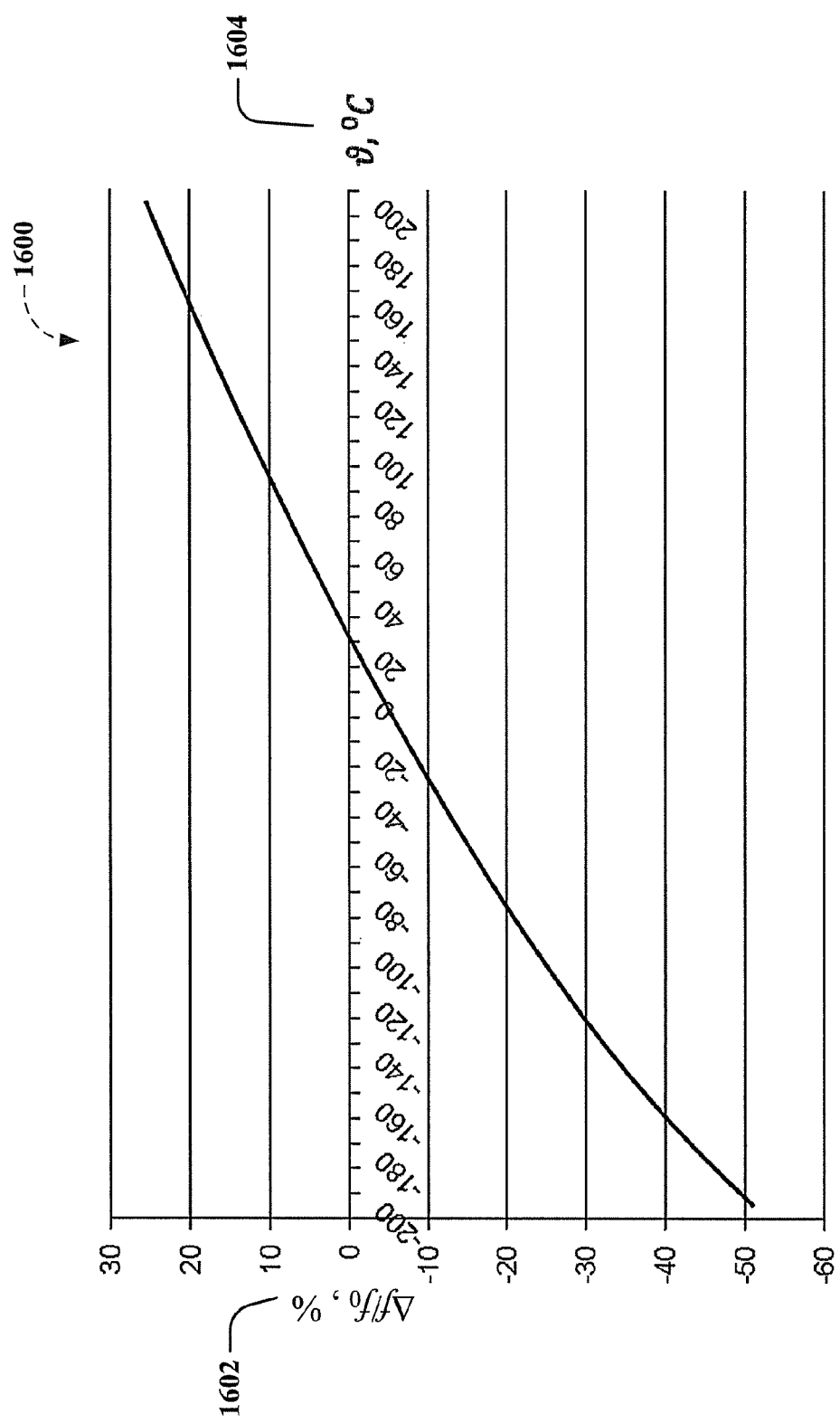
FIG. 16 depicts frequency variation of a Helmholtz resonator over the range of temperatures, according to further non-limiting aspects of the subject disclosure.

For example, FIG. 16 depicts frequency variation 1602 ($\Delta f/f_o$) of a Helmholtz resonator over a range of temperatures, according to further non-limiting aspects of the subject disclosure. As depicted in FIG. 16, resonance frequency of a Helmholtz resonator can be employed to determine temperatures, according to non-limiting aspects of various embodiments as described herein. As a non-limiting example, assuming an initial frequency, $f_o=20$ KHz at 27° C., a change in temperature, $\Delta\theta=1°$ C., could result in a change in frequency, $\Delta f=35$ Hz, whereas a change in temperature, $\Delta\theta=0.1°$ C., could result in a change in frequency, $\Delta f=3.5$ Hz, according to FIG. 16.

Figure 17:
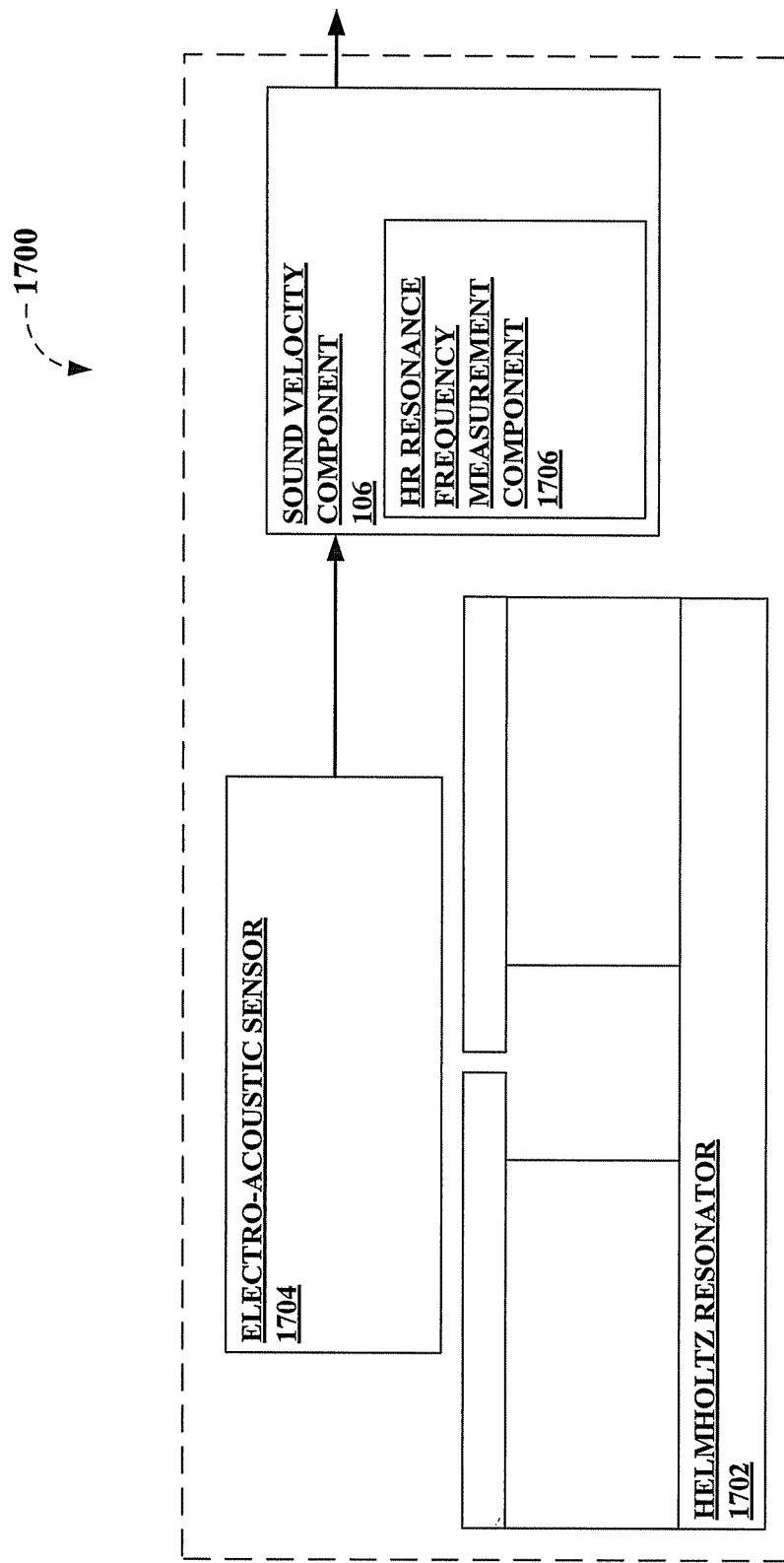
FIG. 17 depicts a Helmholtz resonator as part of an electro-acoustic sensor, according to non-limiting aspects of the subject disclosure.

Accordingly, in various non-limiting embodiments, the subject disclosure facilitates employing a Helmholtz resonator for temperature measurement. For instance, FIG. 17 depicts a Helmholtz resonator 1702 as part of an electro-acoustic sensor 1704, according to non-limiting aspects of the subject disclosure. Electro-acoustic sensor 1704 can provide a signal to sound velocity component 106 to facilitate determination of sound velocity. For example, sound velocity component 106 can comprise a HR resonance frequency measurement component 1706 configured to determine a frequency of resonance associated with Helmholtz resonator 1702 at particular environmental conditions of interest. Thus, sound velocity component 106, can determine a sound velocity based on a resonance frequency determined by HR resonance frequency measurement component 1706, according to the relationship given in Eqn. (7), for example. In a non-limiting aspect, HR resonance frequency measurement component 1706 can employ various techniques for determining a resonance frequency of a signal associated with Helmholtz resonator 1702, including, but not limited to, self excitation/oscillation or free-running oscillator employing a frequency counter that measures frequency or a voltage controlled oscillator input of a phase locked loop locked to the oscillator and an analog-to-digital converter, frequency, speed, and impedance magnitude determination, phase or group delay measurement, determination of impedance magnitude using wideband noise, zero-crossing counting in a decay pulse response, frequency locked loop, period counting, self-mixing with delay, and/or combinations thereof. Based on determination of sound velocity by sound velocity component 106, various embodiments described herein can determine temperature, for example, according to the relationship given in Eqn. (10).

Figure 18:
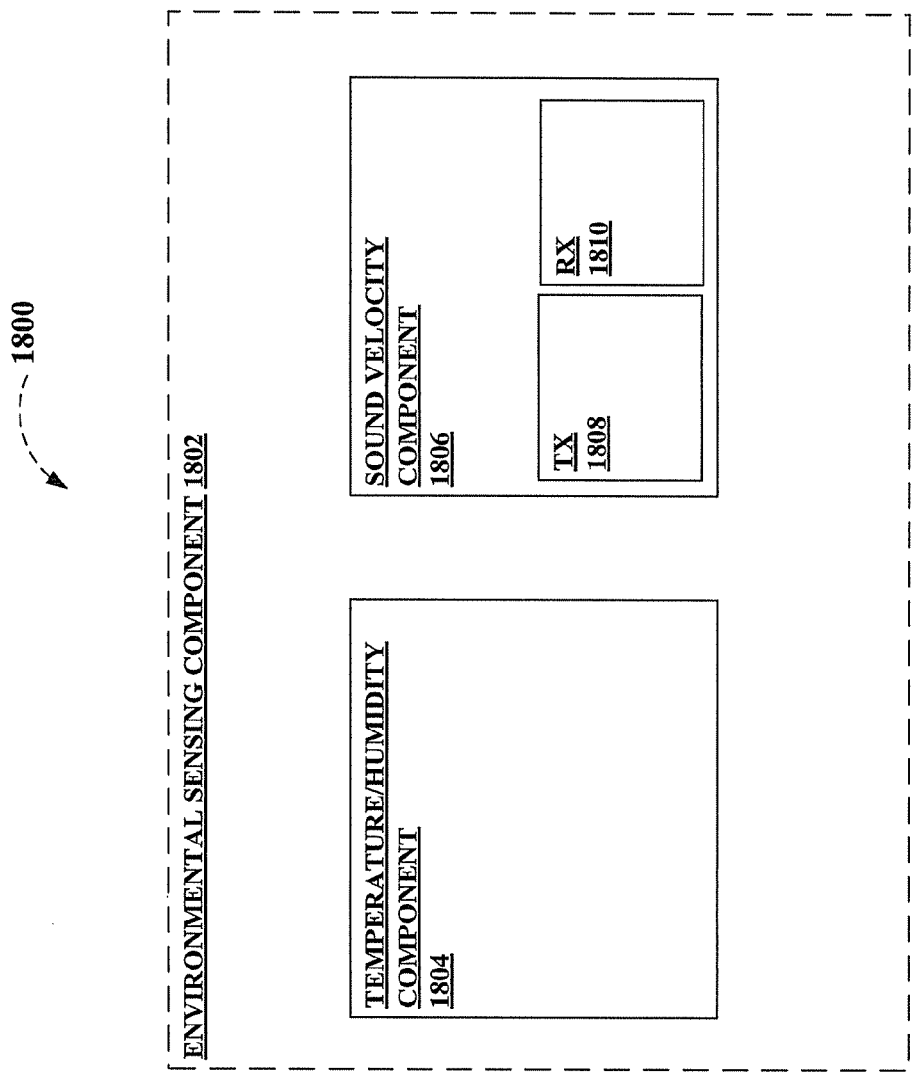
FIG. 18 depicts an exemplary embodiment of a system configured to determine ambient temperatures and/or relative humidity, in which non-limiting aspects of the subject disclosure can be practiced.

FIG. 18 depicts an exemplary embodiment of a system 1800 configured to determine ambient temperatures and/or relative humidity, in which non-limiting aspects of the subject disclosure can be practiced. System 1800 and/or portions or components thereof can be integrated or associated with an electronic device such as a mobile device, for example, as further described herein, regarding exemplary operating environments 400 and/or exemplary sensor 406 of FIG. 4. System 1800 can comprise an environmental sensing component 1802, which can comprise one or more of a temperature and/or humidity component 1804 and/or a sound velocity component 1806. Temperature and/or humidity component 1804 can comprise temperature and/or humidity sensors such as described above regarding environmental sensor 904 of exemplary MEMS device 900. Accordingly, temperature and/or humidity component 1804 can determine temperature and/or humidity inside an enclosure such as for internal environmental conditions in encasement or enclosure 402 associated with exemplary sensor 406 (e.g., at exemplary sensing point 412). Sound velocity component 1806 can comprise or be associated with a transmitter, Tx 1808 (e.g., transmitter 1006, a speaker, etc.), synchronized with a receiver, Rx 1810 (e.g., receiver 1010, a microphone, etc.), and configured to transmit a coded signal to the receiver 1810 over a known or predetermined distance (e.g., acoustic path 1014), for example, as further described above regarding FIGS. 10-11. Sound velocity component 1806 can be configured to determine the time of flight from the transmitter, Tx 1808, to the receiver, Rx 1810, associated with the coded signal over the known or predetermined distance (e.g., acoustic path 1014). In turn, sound velocity component 1806 can be further configured to determine ambient sound velocity, as further described herein, for example, regarding Eqn. (6). Accordingly, environmental sensing component 1802 can be configured to determine ambient temperature and/or relative humidity, e.g., at exemplary operating point 302, according to techniques described herein, for example, regarding FIGS. 2-8 employing absolute humidity.

As a non-limiting example, transmitter, Tx 1808, and receiver, Rx 1810, can comprise or be associated with ultrasound transmitters, Tx 1808, and receivers, Rx 1810. As a further non-limiting example, an exemplary ultrasound transmitter, Tx 1808, can comprise a speaker operating at the ultrasound frequency (>25 KHz), an ultrasound transducer, such as piezoelectric micromachined ultrasonic transducers (PMUT) and/or capacitive micromachined ultrasonic transducers (CMUT), piezo-ceramic actuators based on lead zirconate titanate (PZT) or quartz. In yet another non-limiting example, an ultrasound receiver, Rx 1810, can comprise a microphone having extended band to near-audio ultrasound.

Figure 19:
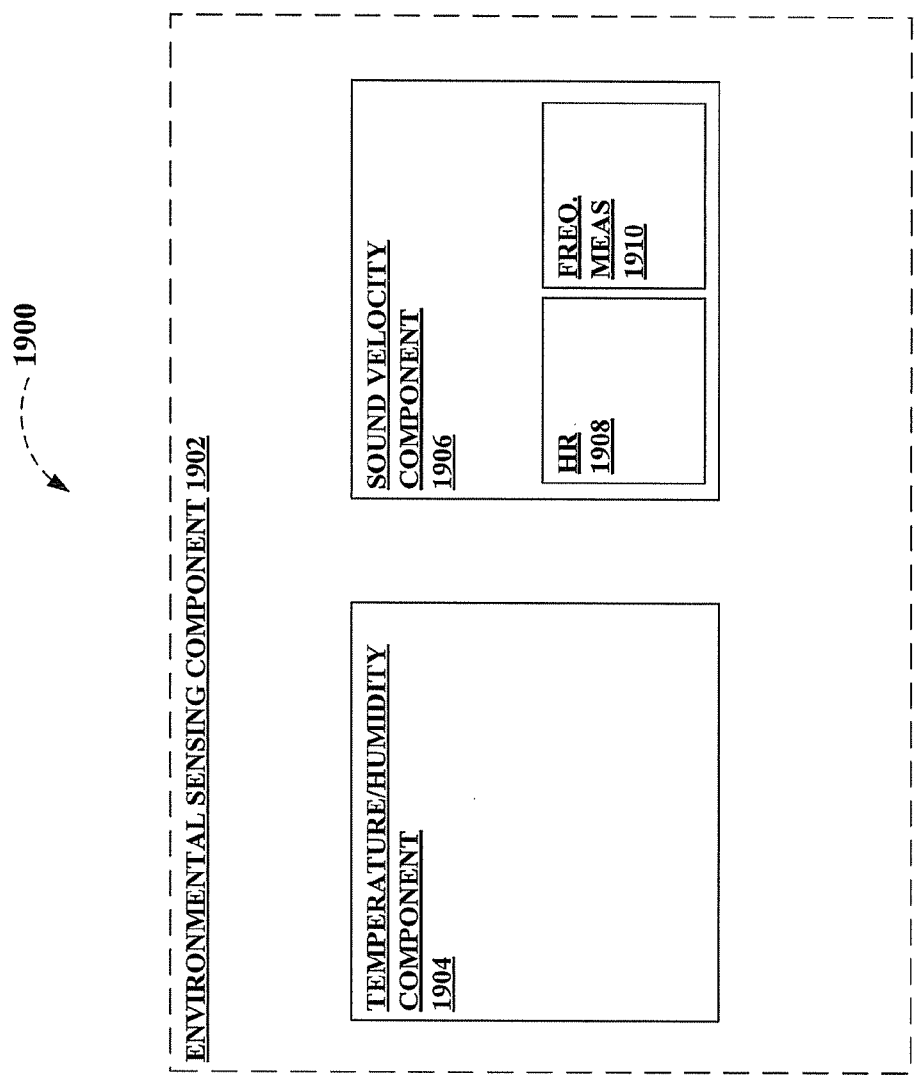
FIG. 19 depicts another exemplary embodiment of a system configured to determine ambient temperatures and/or relative humidity, in which further non-limiting aspects of the subject disclosure can be practiced.

FIG. 19 depicts an exemplary embodiment of a system 1900 configured to determine ambient temperatures and/or relative humidity, in which non-limiting aspects of the subject disclosure can be practiced. System 1900 and/or portions or components thereof can be integrated or associated with an electronic device such as a mobile device, for example, as further described herein, regarding exemplary operating environments 400 and/or exemplary sensor 406 of FIG. 4. System 1900 can comprise an environmental sensing component 1902, which can comprise one or more of a temperature and/or humidity component 1904 and/or a sound velocity component 1906. Temperature and/or humidity component 1904 can comprise temperature and/or humidity sensors such as described above regarding environmental sensor 904 of exemplary MEMS device 900. Accordingly, temperature and/or humidity component 1904 can determine temperature and/or humidity inside an enclosure such as for internal environmental conditions in encasement or enclosure 402 associated with exemplary sensor 406 (e.g., at exemplary sensing point 412). Sound velocity component 1906 can further comprise or be associated with a Helmholtz resonator, HR 1908 (e.g., Helmholtz resonator 1202/1302/1402/1702, electro-acoustic sensor 1704, etc.), configured to provide a signal to sound velocity component 106 to facilitate determination of sound velocity, for example, as further described above regarding FIGS. 12-14 and 17. Sound velocity component 1906 can further comprise or be associated with a frequency measurement component 1910 (e.g., by HR resonance frequency measurement component 1706, etc.) configured to determine the resonance frequency associated with HR 1908, for example, as further described above. In a non-limiting aspect, sound velocity component 1906 can be further configured to determine a sound velocity based on a resonance frequency determined by frequency measurement component 1910, according to the relationship given in Eqn. (7). In turn, based on determination of sound velocity by sound velocity component 1906, various non-limiting embodiments can determine temperature as described herein, for example, according to the relationship given in Eqn. (10). As a non-limiting example, sound velocity component 1906, environmental sensing component 1902, and/or portions or combinations thereof, can be configured to determine ambient temperature directly according to the relationship given in Eqn. (10).

Accordingly, in various non-limiting embodiments, systems, apparatuses, and the like can be configured to determine ambient temperatures and/or ambient relative humidity, according to various aspects of the subject disclosure described herein. As a non-limiting example, an exemplary system, apparatuses, and/or portions thereof, etc. can comprise a memory to store computer-executable components and a processor communicatively coupled to the memory that facilitates execution of the computer-executable components. As a non-limiting example, an exemplary system, apparatuses, and/or portions thereof, etc. can comprise or be associated with an exemplary portable communication device such as, for example, exemplary mobile device 2200 of FIG. 22 and/or components or portions thereof, to facilitate various non-limiting aspects of the subject disclosure. In addition, exemplary systems, apparatuses, and/or portions thereof, etc. can comprise a sound velocity component (e.g., sound velocity component 106, sound velocity component 1806, sound velocity component 1906, etc.) within an encasement (e.g., encasement or enclosure 402, etc.) and configured to determine ambient sound velocity external to the encasement (e.g., at exemplary operating point 302). Exemplary systems, apparatuses, and/or portions thereof, etc. can further comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the encasement (e.g., at exemplary operating point 302) based in part on the ambient sound velocity.

In a non-limiting example, sound velocity component (e.g., sound velocity component 106, sound velocity component 1806, sound velocity component 1906, etc.) can comprise a receiver (e.g., Rx 1810, receiver 1010, a microphone, etc.) and a transmitter (e.g., Tx 1808, transmitter 1006, a speaker, etc.) configured to transmit a coded ultrasonic acoustic signal to the receiver (e.g., Rx 1810, receiver 1010, a microphone, etc.), for example, as further described above regarding FIGS. 10-11 and 18. In a further non-limiting aspect, the receiver (e.g., Rx 1810, receiver 1010, a microphone, etc.) can be further configured to receive the coded ultrasonic acoustic signal, for example, as further described above regarding FIGS. 10-11 and 18. In addition, sound velocity component (e.g., sound velocity component 106, sound velocity component 1806, sound velocity component 1906, etc.) can be further configured to determine the ambient sound velocity, for example, based on a determined time of flight 1102 of the coded ultrasonic acoustic signal over a predetermined acoustic path length (e.g., acoustic path 1014).

In another non-limiting example, sound velocity component (e.g., sound velocity component 106, sound velocity component 1806, sound velocity component 1906, etc.) can comprise or be associated with a Helmholtz resonator (e.g., HR 1908 Helmholtz resonator 1202/1302/1402/1702, electro-acoustic sensor 1704, and/or components or portions thereof, etc.) within the encasement (e.g., encasement or enclosure 402, etc.). In a further non-limiting aspect, sound velocity component (e.g., sound velocity component 106, sound velocity component 1806, sound velocity component 1906, etc.) can be further configured to determine the ambient temperature external to the encasement as a linear function of the ambient sound velocity (e.g., at exemplary operating point 302).

As a further non-limiting example, an exemplary apparatus, system, and/or portions thereof, etc. can comprise a memory to store computer-executable components and a processor communicatively coupled to the memory that facilitates execution of the computer-executable components. In a non-limiting example, an exemplary apparatus, system, and/or portions thereof, etc. can comprise or be associated with an exemplary portable communication device such as, for example, exemplary mobile device 2200 of FIG. 22 and/or components or portions thereof, to facilitate various non-limiting aspects of the subject disclosure. In addition, an exemplary apparatus, system, and/or portions thereof, etc. can comprise a sound velocity component (e.g., sound velocity component 106, sound velocity component 1806, sound velocity component 1906, etc.) comprising a Helmholtz resonator (e.g., HR 1908 Helmholtz resonator 1202/1302/1402/1702, electro-acoustic sensor 1704, and/or components or portions thereof, etc.) within an encasement (e.g., encasement or enclosure 402, etc.) and configured to determine sound velocity external to the encasement (e.g., at exemplary operating point 302) based on resonance frequency of the Helmholtz resonator. In another non-limiting aspect, an exemplary apparatus, system, and/or portions thereof, etc. can further comprise one or more of a temperature sensor or a humidity sensor within the encasement, for example, as further described above regarding FIGS. 4 and 9, and/or environmental sensor 904 of exemplary MEMS device 900. In yet another non-limiting aspect, an exemplary apparatus, system, and/or portions thereof, etc. can also comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the encasement (e.g., at exemplary operating point 302) based on the ambient sound velocity. In a non-limiting aspect, the environmental sensing component of an exemplary apparatus, system, and/or portions thereof, etc. can be further configured to determine the ambient temperature external to the encasement as a linear function of the ambient sound velocity, for example, as further described above regarding FIG. 15 and Eqns. (8)-(10). In still further non-limiting aspects, environmental sensing component (e.g., environmental sensing component 102, environmental sensing component 1802, environmental sensing component 1902, etc.) can be further configured to calibrate the temperature sensor (e.g., temperature sensor as further described above regarding FIGS. 4 and 9, and/or environmental sensor 904 of exemplary MEMS device 900, etc.), for example, based on a determination of the ambient temperature.

In yet another non-limiting example, an exemplary apparatus, system, and/or portions thereof, etc. can comprise a memory to store computer-executable components and a processor communicatively coupled to the memory that facilitates execution of the computer-executable components. In a non-limiting example, an exemplary apparatus, system, and/or portions thereof, etc. can comprise or be associated with an exemplary portable communication device such as, for example, exemplary mobile device 2200 of FIG. 22 and/or components or portions thereof, to facilitate various non-limiting aspects of the subject disclosure. In addition, an exemplary apparatus, system, and/or portions thereof, etc. can comprise a temperature sensor and a humidity sensor within an encasement (e.g., encasement or enclosure 402, etc.) configured to sense temperature and humidity within the encasement, for example, as further described above regarding FIGS. 4 and 9, and/or environmental sensor 904 of exemplary MEMS device 900, according to non-limiting aspect. Exemplary apparatus, system, and/or portions thereof, etc. can further comprise a sound velocity component (e.g., sound velocity component 106, sound velocity component 1806, sound velocity component 1906, etc.) comprising a transmitter (e.g., Tx 1808, transmitter 1006, a speaker, etc.) configured to transmit a coded ultrasonic acoustic signal to a receiver (e.g., Rx 1810, receiver 1010, a microphone, etc.), wherein the sound velocity component is further configured to determine ambient sound velocity external to the enclosure based on a determined time of flight 1102 of the coded ultrasonic acoustic signal over a predetermined acoustic path length (e.g., acoustic path 1014) between the transmitter and receiver, according to further non-limiting aspects as described above, for example, regarding FIGS. 10-11. In other non-limiting aspects, exemplary apparatus, system, and/or portions thereof, etc. can further comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the encasement (e.g., at exemplary operating point 302) based on the ambient sound velocity and the temperature and the humidity within the encasement (e.g., at exemplary sensing point 412). In still further non-limiting aspects, environmental sensing component (e.g., environmental sensing component 102, environmental sensing component 1802, environmental sensing component 1902, etc.) can be further configured to calibrate the temperature sensor (e.g., temperature sensor as further described above regarding FIGS. 4 and 9, and/or environmental sensor 904 of exemplary MEMS device 900, etc.), for example, based on a determination of the ambient temperature.

In still further non-limiting implementations, an exemplary device according to various aspects of the subject disclosure can comprise a means for sensing (e.g., as further described above regarding FIGS. 4 and 9, and/or environmental sensor 904 of exemplary MEMS device 900, etc.) one or more of temperature or humidity within an encasement (e.g., encasement or enclosure 402, etc.), such as at exemplary sensing point 412. In further non-limiting aspect, an exemplary device can further comprise means for determining sound velocity external to the encasement, based on one or more measurement means located within the encasement. As a non-limiting example, exemplary measurement means can comprise one or more of one of a Helmholtz resonator (e.g., HR 1908 Helmholtz resonator 1202/1302/1402/1702, electro-acoustic sensor 1704, and/or components or portions thereof, etc.), an ultrasonic transmitter (e.g., Tx 1808, transmitter 1006, a speaker, etc.), or a receiving means (e.g., Rx 1810, receiver 1010, a microphone, etc.) configured to accept an ultrasonic acoustic signal.

In a further non-limiting example, exemplary means for determining sound velocity can comprise various non-limiting embodiments, and/or components or portions thereof described above regarding FIGS. 9-15 and 18-19, such as those described regarding exemplary sound velocity components (e.g., sound velocity component 106, sound velocity component 1806, sound velocity component 1906, etc.). In addition, an exemplary device can further comprise means for determining one or more of temperature or relative humidity external to the encasement (e.g., at exemplary operating point 302). As a non-limiting example, exemplary means for determining one or more of temperature or relative humidity external to the increasing can comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the enclosure (e.g., at exemplary operating point 302) based on the sound velocity external to the encasement and the temperature and the humidity within the encasement (e.g., at exemplary sensing point 412).

In addition, in a further non-limiting aspect, one or more of the means for sensing, the means for determining sound velocity, the measurement means, and/or the means for determining temperature or relative humidity, and/or portions thereof, associated with an exemplary device can comprise, in part, a memory to store computer-executable components and/or a processor communicatively coupled to the memory that facilitates execution of the computer-executable components. In a non-limiting example, one or more of the means for sensing, the means for determining sound velocity, the measurement means, and/or the means for determining temperature or relative humidity, and/or portions thereof, associated with an exemplary device can comprise or be associated with exemplary mobile device 2200 of FIG. 22 and/or components or portions thereof, to facilitate various non-limiting aspects of the subject disclosure.

Figure 20:
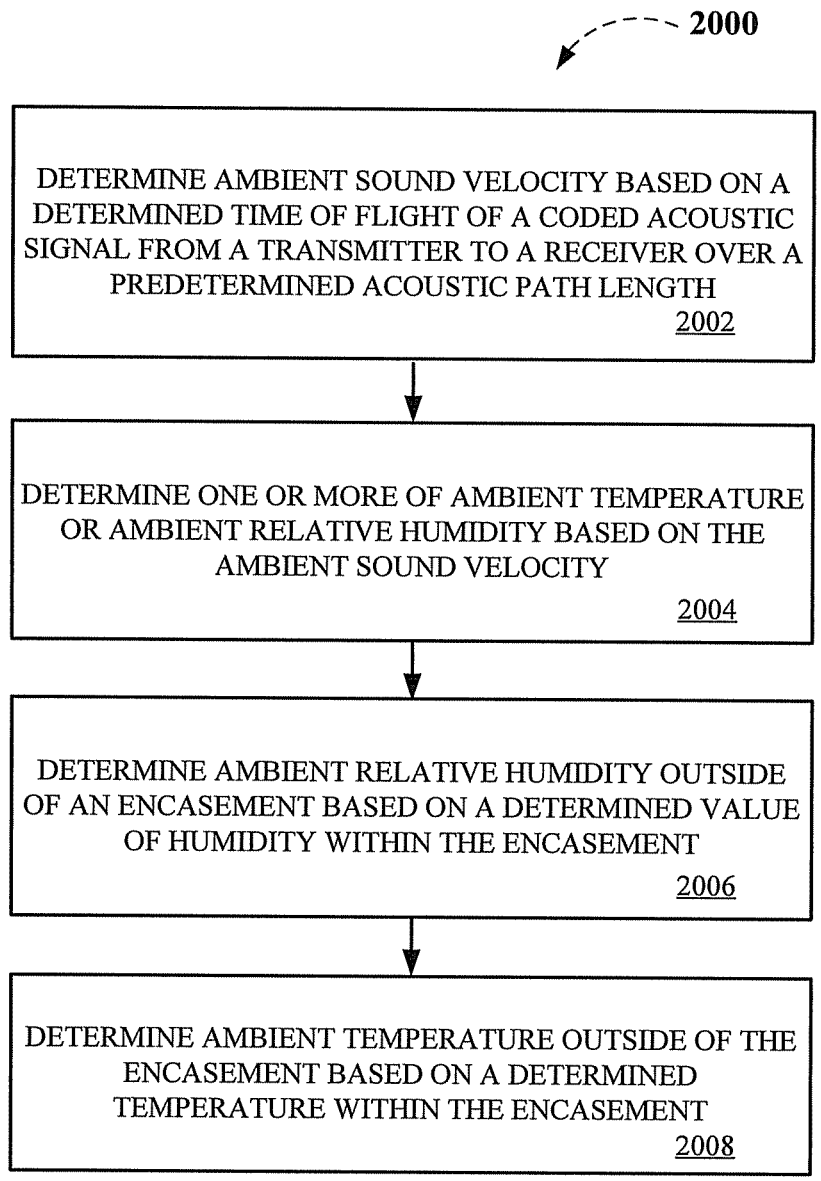
FIG. 20 provides a non-limiting flow diagram of exemplary methods according to various non-limiting aspects as described herein.
Figure 21:
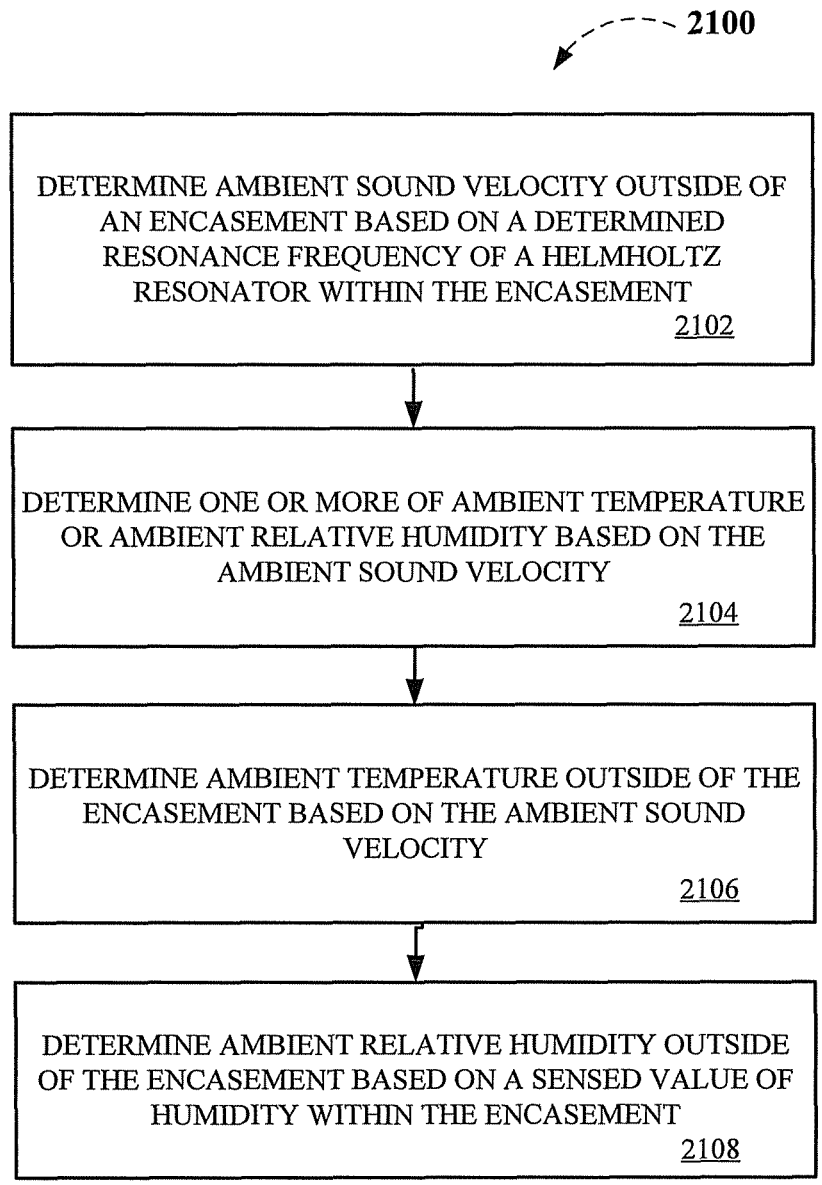
FIG. 21 provides another non-limiting flow diagram of exemplary methods according to further non-limiting aspects as described herein.

In view of the subject matter described supra, methods that can be implemented in accordance with the subject disclosure will be better appreciated with reference to the flowcharts of FIGS. 20-21. While for purposes of simplicity of explanation, the methods are shown and described as a series of blocks, it is to be understood and appreciated that such illustrations or corresponding descriptions are not limited by the order of the blocks, as some blocks may occur in different orders and/or concurrently with other blocks from what is depicted and described herein. Any non-sequential, or branched, flow illustrated via a flowchart should be understood to indicate that various other branches, flow paths, and orders of the blocks, can be implemented which achieve the same or a similar result. Moreover, not all illustrated blocks may be required to implement the methods described hereinafter.

Exemplary Methods

FIG. 20 provides a non-limiting flow diagram of exemplary methods 2000 according to various non-limiting aspects as described herein. For instance, at 2002, exemplary methods 2000 can comprise determining, by a system in an encasement (e.g., encasement or enclosure 402, etc.)

comprising a processor, ambient sound velocity. As a non-limiting example, an exemplary system can comprise or be associated with an exemplary portable communication device such as, for example, exemplary mobile device 2200 of FIG. 22 and/or components or portions thereof, to facilitate various non-limiting aspects of the subject disclosure. In addition, exemplary systems can comprise a sound velocity component (e.g., sound velocity component 106, sound velocity component 1806, sound velocity component 1906, etc.) configured to determine ambient sound velocity (e.g., at exemplary operating point 302). For instance, as described above, sound velocity component (e.g., sound velocity component 106, sound velocity component 1806, sound velocity component 1906, etc.) can comprise a transmitter (e.g., Tx 1808, transmitter 1006, a speaker, etc.) configured to transmit a coded ultrasonic acoustic signal to a receiver (e.g., Rx 1810, receiver 1010, a microphone, etc.), for example, as further described above regarding FIGS. 10-11 and 18. In a further non-limiting aspect, the receiver (e.g., Rx 1810, receiver 1010, a microphone, etc.) can be further configured to receive the coded ultrasonic acoustic signal, for example, as further described above regarding FIGS. 10-11 and 18. In addition, sound velocity component (e.g., sound velocity component 106, sound velocity component 1806, sound velocity component 1906, etc.) can be further configured to determine the ambient sound velocity, for example, based on a determined time of flight 1102 of the coded ultrasonic acoustic signal over a predetermined acoustic path length (e.g., acoustic path 1014). Thus, at 2002, exemplary methods 2000 can comprise determining, by the system, the ambient sound velocity based on a determined time of flight of a coded acoustic signal (e.g., an ultrasonic acoustic signal, etc.) from a transmitter to a receiver over a predetermined acoustic path length.

In addition, at 2004, exemplary methods 2000 can comprise determining, by the system, one or more of ambient temperature or ambient relative humidity based on the ambient sound velocity. As a non-limiting example, exemplary systems can comprise an environmental sensing component (e.g., environmental sensing component 102, environmental sensing component 1802, environmental sensing component 1902, etc.) within an encasement (e.g., encasement or enclosure 402, etc.) and configured to determine one or more of an ambient temperature or an ambient relative humidity external to the encasement (e.g., at exemplary operating point 302) based in part on the ambient sound velocity, as further described above. Thus, the determining the ambient sound velocity at 2002 and determining the ambient temperature or the ambient relative humidity at 2004 can comprise determining the ambient sound velocity and determining the ambient temperature or the ambient relative humidity by the system comprising at least a portion of an exemplary portable communication device such as, for example, exemplary mobile device 2200 of FIG. 22 and/or components or portions thereof.

Thus, at 2006 exemplary methods 2000 can comprise determining, by the system, the ambient relative humidity outside of the encasement based on a determined value of humidity within the encasement. For instance, as described above, an exemplary system can comprise a temperature sensor and/or a humidity sensor within an encasement (e.g., encasement or enclosure 402, etc.) configured to sense temperature and humidity within the encasement, for example, as further described above regarding FIGS. 4 and 9, and/or environmental sensor 904 of exemplary MEMS device 900, according to non-limiting aspect. Thus, as further described above, exemplary systems can comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the encasement (e.g., at exemplary operating point 302) based on the ambient sound velocity and the temperature and the humidity within the encasement (e.g., at exemplary sensing point 412). Accordingly, at 2008 exemplary methods 2000 can also comprise determining, by the system, the ambient temperature outside of the encasement based on a determined temperature within the encasement.

FIG. 21 provides another non-limiting flow diagram 2100 of exemplary methods according to further non-limiting aspects as described herein. For instance, at 2102, exemplary methods 2100 can comprise determining, by a system comprising a processor, ambient sound velocity. As a non-limiting example, an exemplary system can comprise or be associated with exemplary mobile device 2200 of FIG. 22 and/or components or portions thereof, to facilitate various non-limiting aspects of the subject disclosure. In addition, exemplary systems can comprise a sound velocity component (e.g., sound velocity component 106, sound velocity component 1806, sound velocity component 1906, etc.) configured to determine ambient sound velocity (e.g., at exemplary operating point 302). For instance, as described above, sound velocity component (e.g., sound velocity component 106, sound velocity component 1806, sound velocity component 1906, etc.) can comprise or be associated with a Helmholtz resonator (e.g., HR 1908 Helmholtz resonator 1202/1302/1402/1702, electro-acoustic sensor 1704, and/or components or portions thereof, etc.) within an encasement (e.g., encasement or enclosure 402, etc.). Thus, at 2102, exemplary methods 2100 can comprise determining, by the system, the ambient sound velocity outside of an encasement based on a determined resonance frequency of a Helmholtz resonator within the encasement.

In addition, at 2104, exemplary methods 2100 can comprise determining, by the system, one or more of ambient temperature or ambient relative humidity based on the ambient sound velocity. As a non-limiting example, exemplary systems can comprise an environmental sensing component (e.g., environmental sensing component 102, environmental sensing component 1802, environmental sensing component 1902, etc.) within an encasement (e.g., encasement or enclosure 402, etc.) and configured to determine one or more of an ambient temperature or an ambient relative humidity external to the encasement (e.g., at exemplary operating point 302) based in part on the ambient sound velocity, as further described above. Accordingly, in a further non-limiting aspect, sound velocity component (e.g., sound velocity component 106, sound velocity component 1806, sound velocity component 1906, etc.) can be further configured to determine the ambient temperature external to the encasement based on the ambient sound velocity (e.g., at exemplary operating point 302), such as a linear function of the ambient sound velocity, at 2106.

In addition, at 2106 exemplary methods 2100 can comprise determining, by the system, the ambient relative humidity outside of the encasement based on a determined value of humidity within the encasement. For instance, as described above, an exemplary system can comprise a temperature sensor and/or a humidity sensor within an encasement (e.g., encasement or enclosure 402, etc.) configured to sense temperature and humidity within the encasement, for example, as further described above regarding FIGS. 4 and 9, and/or environmental sensor 904 of exemplary MEMS device 900, according to non-limiting aspect. Thus, as further described above, exemplary systems can comprise an environmental sensing component (e.g., environmental sensing component 102, environmental sensing component 1802, environmental sensing component 1902, etc.) within the encasement (e.g., encasement or enclosure 402, etc.) and configured to determine one or more of an ambient temperature or an ambient relative humidity external to the encasement (e.g., at exemplary operating point 302) based on the ambient sound velocity and the temperature and the humidity within the encasement (e.g., at exemplary sensing point 412).

Exemplary Mobile Device

Figure 22:
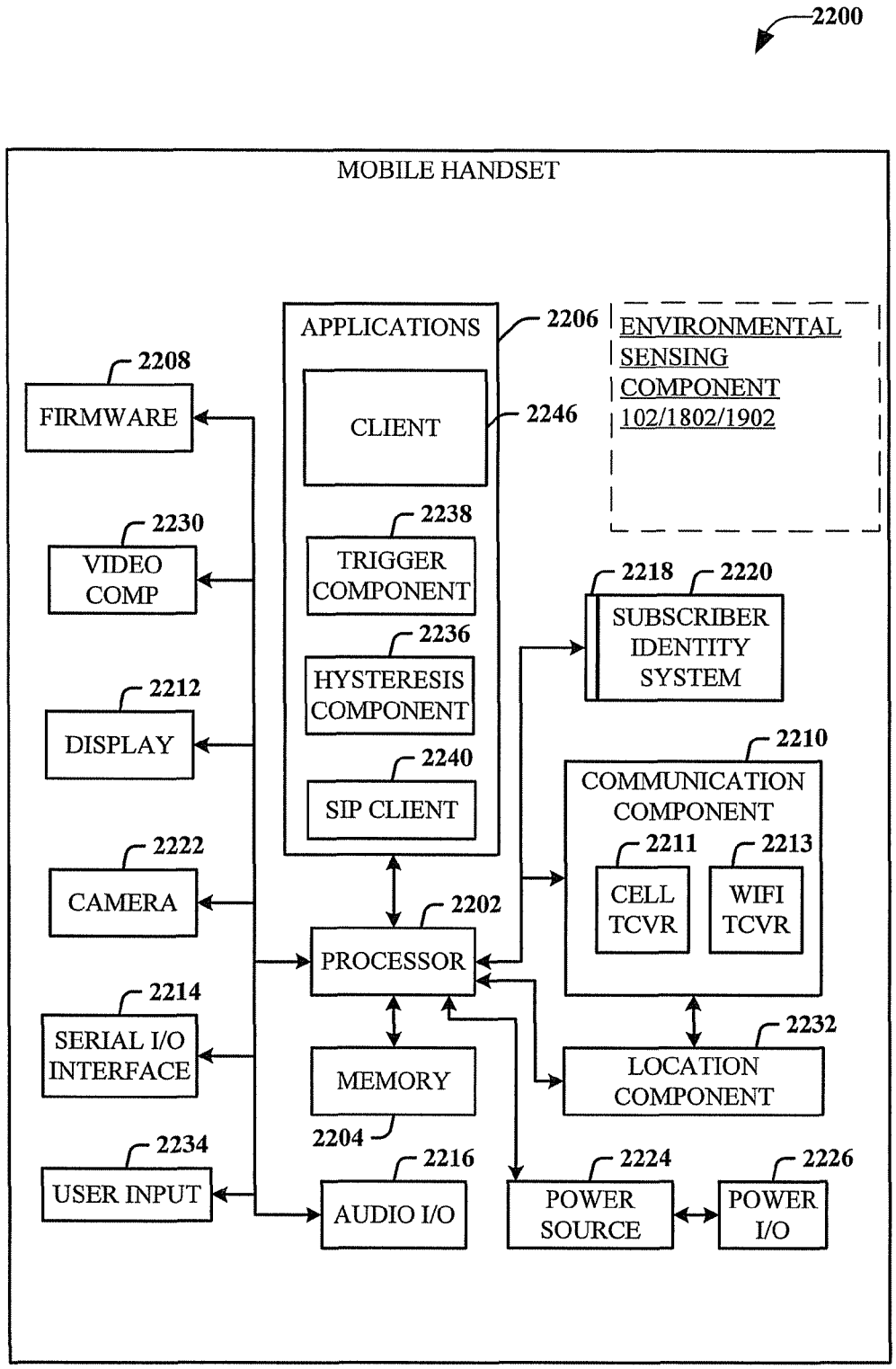
FIG. 22 illustrates a schematic diagram of an exemplary mobile device (e.g., a mobile handset) that can facilitate various non-limiting aspects of the subject disclosure in accordance with the embodiments described herein.

FIG. 22 depicts a schematic diagram of an exemplary mobile device 2200 (e.g., a mobile handset) that can facilitate various non-limiting aspects of the subject disclosure in accordance with the embodiments described herein. Accordingly, exemplary mobile device can comprise or be associated with environmental sensing component 102, 1802, 1902, and/or portions or combinations thereof, as well as other disclosed components, devices, features, functionality, logic configured according to provided algorithms, portions thereof, and so on, without limitation. Although mobile handset 2200 is illustrated herein, it will be understood that other devices, whether mobile devices or otherwise, can facilitate various non-limiting aspects of the subject disclosure. In accordance with the embodiments described herein, exemplary devices suitable for performing various aspects described herein can include, without limitation, a sensor package and/or associated signal processing components such as ASICs and the like, a desktop computer, a cellular phone, a laptop computer, a tablet personal computer (PC) device, and/or a personal digital assistant (PDA), or other mobile device, and so on. As further examples, exemplary devices suitable for performing various aspects described herein can include, without limitation, cameras, global positioning system (GPS) devices, and other such devices as a pen computing device, portable digital music player, home entertainment devices, network capable devices, appliances, kiosks, and sensors, and so on. It is to be understood that exemplary mobile device 2200 can comprise more or less functionality than those exemplary devices described above, as the context requires, and as further described herein.

For instance, mobile handset 2200 is merely illustrated to provide context for the embodiments of the subject matter described herein. The following discussion is intended to provide a brief, general description of an example of a suitable environment 2200 in which the various embodiments can be implemented. While the description includes a general context of computer-executable instructions embodied on a non-transitory computer readable storage medium, those skilled in the art will recognize that the subject matter also can be implemented in combination with other program modules or components and/or as a combination of hardware and software.

Generally, applications (e.g., program modules) can include routines, programs, components, data structures, etc., that perform particular tasks or implement particular abstract data types. Moreover, those skilled in the art will appreciate that the methods described herein can be practiced with other system configurations, including single-processor or multiprocessor systems, minicomputers, mainframe computers, as well as personal computers, hand-held computing devices, microprocessor-based or programmable consumer electronics, and the like, each of which can be operatively coupled to one or more associated devices.

A computing device can typically include a variety of computer-readable media. Computer readable media can comprise any available media that can be accessed by the computer and includes both volatile and non-volatile media, removable and non-removable media. By way of example and not limitation, computer-readable media can comprise computer storage media and communication media. Computer storage media can include volatile and/or non-volatile media, removable and/or non-removable media implemented in any method or technology for storage of information, such as computer-readable instructions, data structures, program modules, or other data. Computer storage media can include, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules, or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable communications media as distinguishable from computer-readable storage media.

The handset 2200 can include a processor 2202 for controlling and processing all onboard operations and functions. A memory 2204 interfaces to the processor 2202 for storage of data and one or more applications 2206 (e.g., communications applications such as IM, SMS, adaptable to electronic payments as described herein and/or other application specifically targeted to electronic payments for transfers, such as MTMS, etc.). The applications 2206 can be stored in the memory 2204 and/or in a firmware 2208, and executed by the processor 2202 from either or both the memory 2204 or/and the firmware 2208. The firmware 2208 can also store startup code for execution in initializing the handset 2200. A communications component 2210 interfaces to the processor 2202 to facilitate wired/wireless communication with external systems, e.g., cellular networks, VoIP networks, and so on. Here, the communications component 2210 can also include a suitable cellular transceiver 2211 (e.g., a GSM transceiver) and/or an unlicensed transceiver 2213 (e.g., Wireless Fidelity (WiFi™), Worldwide Interoperability for Microwave Access (WiMax®)) for corresponding signal communications. The communications component 2210 also facilitates communications reception from terrestrial radio networks (e.g., broadcast), digital satellite radio networks, and Internet-based radio services networks.

The handset 2200 includes a display 2212 for displaying text, images, video, telephony functions (e.g., a Caller ID function), setup functions, and for user input. For example, the display 2212 can also be referred to as a "screen" that can accommodate the presentation of multimedia content (e.g., music metadata, messages, wallpaper, graphics, etc.). The display 2212 can also display videos and can facilitate the generation, editing and sharing of video quotes. A serial I/O interface 2214 is provided in communication with the processor 2202 to facilitate wired and/or wireless serial communications (e.g., Universal Serial Bus (USB), and/or Institute of Electrical and Electronics Engineers (IEEE) 2394) through a hardwire connection, and other serial input devices (e.g., a keyboard, keypad, and mouse). This supports updating and troubleshooting the handset 2200, for example. Audio capabilities are provided with an audio I/O component 2216, which can include a speaker for the output of audio signals related to, for example, indication that the user pressed the proper key or key combination to initiate the user feedback signal. The audio I/O component 2216 also facilitates the input of audio signals through a microphone to record data and/or telephony voice data, and for inputting voice signals for telephone conversations.

The handset 2200 can include a slot interface 2218 for accommodating a SIC (Subscriber Identity Component) in the form factor of a card Subscriber Identity Module (SIM) or universal SIM 2220, and interfacing the SIM card 2220 with the processor 2202. However, it is to be appreciated that the SIM card 2220 can be manufactured into the handset 2200, and updated by downloading data and software.

The handset 2200 can process Internet Protocol (IP) data traffic through the communication component 2210 to accommodate IP traffic from an IP network such as, for example, the Internet, a corporate intranet, a home network, a person area network, etc., through an ISP or broadband cable provider. Thus, VoIP traffic can be utilized by the handset 2200 and IP-based multimedia content can be received in either an encoded or a decoded format.

A video processing component 2222 (e.g., a camera) can be provided for decoding encoded multimedia content. The video processing component 2222 can aid in facilitating the generation and/or sharing of video. The handset 2200 also includes a power source 2224 in the form of batteries and/or an alternating current (AC) power subsystem, which power source 2224 can interface to an external power system or charging equipment (not shown) by a power input/output (I/O) component 2226.

The handset 2200 can also include a video component 2230 for processing video content received and, for recording and transmitting video content. For example, the video component 2230 can facilitate the generation, editing and sharing of video. A location-tracking component 2232 facilitates geographically locating the handset 2200. A user input component 2234 facilitates the user inputting data and/or making selections as previously described. The user input component 2234 can also facilitate selecting perspective recipients for fund transfer, entering amounts requested to be transferred, indicating account restrictions and/or limitations, as well as composing messages and other user input tasks as required by the context. The user input component 2234 can include such conventional input device technologies such as a keypad, keyboard, mouse, stylus pen, and/or touch screen, for example.

Referring again to the applications 2206, a hysteresis component 2236 facilitates the analysis and processing of hysteresis data, which is utilized to determine when to associate with an access point. A software trigger component 2238 can be provided that facilitates triggering of the hysteresis component 2238 when a WiFi™ transceiver 2213 detects the beacon of the access point. A SIP client 2240 enables the handset 2200 to support SIP protocols and register the subscriber with the SIP registrar server. The applications 2206 can also include a communications application or client 2246 that, among other possibilities, can be target for transfer money plugin or user interface component functionality as described above.

The handset 2200, as indicated above related to the communications component 2210, includes an indoor network radio transceiver 2213 (e.g., WiFi transceiver). This function supports the indoor radio link, such as IEEE 802.11, for the dual-mode Global System for Mobile Communications (GSM) handset 2200. The handset 2200 can accommodate at least satellite radio services through a handset that can combine wireless voice and digital radio chipsets into a single handheld device.

It can be understood that while a brief overview of exemplary systems, methods, scenarios, and/or devices has been provided, the disclosed subject matter is not so limited. Thus, it can be further understood that various modifications, alterations, addition, and/or deletions can be made without departing from the scope of the embodiments as described herein. Accordingly, similar non-limiting implementations can be used or modifications and additions can be made to the described embodiments for performing the same or equivalent function of the corresponding embodiments without deviating therefrom.

As used in this application, the terms "component," "module," "device" and "system" can refer to a computer-related entity, either hardware, a combination of hardware and software, software, or software in execution. As one example, a component or module can be, but is not limited to being, a process running on a processor, a processor or portion thereof, a hard disk drive, multiple storage drives (of optical and/or magnetic storage medium), an object, an executable, a thread of execution, a program, and/or a computer. By way of illustration, both an application running on a server and the server can be a component or module. One or more components or modules scan reside within a process and/or thread of execution, and a component or module can be localized on one computer or processor and/or distributed between two or more computers or processors.

As used herein, the term to "infer" or "inference" can refer generally to the process of reasoning about or inferring states of the system, and/or environment from a set of observations as captured via events, signals, and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

In addition, the words "example" or "exemplary" is used herein to mean serving as an example, instance, or illustration. Any aspect or design described herein as "exemplary" is not necessarily to be construed as preferred or advantageous over other aspects or designs. Rather, use of the word, "exemplary," is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

In addition, while an aspect may have been disclosed with respect to only one of several embodiments, such feature may be combined with one or more other features of the other embodiments as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method comprising:
   determining, by a system in an encasement comprising a processor, ambient sound velocity based on a determined time of flight of a coded acoustic signal from a transmitter to a receiver over a predetermined acoustic path length;
   determining, by the system a determined value of humidity within the encasement; and
   determining, by the system, at least one of ambient temperature or ambient relative humidity based at least in part on the ambient sound velocity and the value of the humidity within the encasement.

2. The method of claim 1, wherein the determining the at least one of the ambient temperature or the ambient relative humidity comprises determining, by the system, the ambient temperature outside of the enclosure based at least in part on at least a determined temperature within the enclosure.

3. The method of claim 1, wherein the determining the ambient sound velocity comprises determining, by the system, the ambient sound velocity of an ultrasonic acoustic signal.

4. The method of claim 1, wherein the determining the at least one of the ambient temperature or the ambient relative humidity comprises determining, by the system, the ambient relative humidity outside of the encasement based at least in part on a sensed value of humidity within the encasement.

5. The method of claim 1, wherein the determining the ambient sound velocity and the determining the ambient temperature or the ambient relative humidity comprises determining the ambient sound velocity and determining the ambient temperature or the ambient relative humidity by at least a portion of a portable communication device comprising the system.

6. An apparatus, comprising:
   a memory to store computer-executable components; and
   a processor communicatively coupled to the memory that facilitates execution of the computer-executable components, the computer-executable components, comprising:
   a humidity sensor within an encasement configured to sense humidity within the encasement;
   a sound velocity component comprising a transmitter configured to transmit a coded ultrasonic acoustic signal to a receiver, wherein the sound velocity component is further configured to determine ambient sound velocity external to the encasement based on a determined time of flight of the coded ultrasonic acoustic signal over a predetermined acoustic path length between the transmitter and receiver; and
   an environmental sensing component within the encasement, operatively coupled to the humidity sensor and the sound velocity component, and configured to determine at least one of an ambient temperature or an ambient relative humidity external to the encasement based at least in part on the ambient sound velocity and the humidity within the encasement.

7. The apparatus of claim 6, wherein the environmental sensing component is further configured to calibrate a temperature sensor operatively coupled to the apparatus based at least in part on a determination of the ambient temperature that is determined based on the ambient sound velocity.

* * * * *